(12) United States Patent
Ruch

(10) Patent No.: US 6,833,260 B1
(45) Date of Patent: Dec. 21, 2004

(54) LACTOSE HYDROLYSIS

(75) Inventor: Frank E. Ruch, Falmouth, ME (US)

(73) Assignee: Protein Scientific, Inc., Portland, ME (US)

( * ) Notice: Subject to any disclaimer, the term of this patent is extended or adjusted under 35 U.S.C. 154(b) by 0 days.

(21) Appl. No.: 09/542,121

(22) Filed: Apr. 4, 2000

Related U.S. Application Data

(60) Provisional application No. 60/158,668, filed on Oct. 8, 1999.

(51) Int. Cl.[7] ............................. C12N 9/38; C12N 1/20; C12P 1/00; A23L 1/31
(52) U.S. Cl. ............................... 435/207; 435/4; 435/6; 435/14; 435/41; 435/91.53; 435/99; 435/105; 435/471; 435/252.3; 435/320.1; 435/173.1; 435/243; 435/252.31; 435/262; 435/252.9; 426/56; 426/522; 536/23.2; 536/23.7
(58) Field of Search .......................... 435/4, 6, 14, 41, 435/91.53, 99, 105, 252.9, 232.3, 173.1, 243, 252.31, 262, 471, 69.1, 71.2, 72, 96, 183, 195, 200, 207, 252.3, 320.1, 276; 426/56, 522; 536/23.2–23.7

(56) References Cited

U.S. PATENT DOCUMENTS

| | | |
|---|---|---|
| 3,629,073 A | 12/1971 | Cayle |
| 3,718,739 A | 2/1973 | Cayle |
| 4,016,293 A | 4/1977 | Coughlin et al. |
| 4,141,857 A | 2/1979 | Levy et al. |
| 4,257,884 A | 3/1981 | Lim |
| 4,329,429 A | 5/1982 | Fenton |
| 4,409,247 A | 10/1983 | Baret et al. |
| 4,556,554 A | 12/1985 | Calvo |
| 4,839,419 A | 6/1989 | Kraemer et al. |
| 5,071,763 A | 12/1991 | Somkuti et al. |
| 5,153,128 A | 10/1992 | Nakayama et al. |
| 5,160,745 A | 11/1992 | DeLuca et al. |
| 5,198,351 A | 3/1993 | Somkuti et al. |
| 5,702,723 A | 12/1997 | Griffin |
| 5,736,374 A | 4/1998 | Berka et al. |
| 5,766,907 A | 6/1998 | Chang et al. |
| 5,914,248 A | 6/1999 | Kuipers et al. |

FOREIGN PATENT DOCUMENTS

| | | |
|---|---|---|
| EP | 0006035 | 12/1979 |
| EP | 0 355 036 A1 | 2/1990 |
| EP | 0712935 A | 5/1996 |
| EP | 0228726 A | 7/1997 |
| WO | WO 89/07139 | 8/1989 |
| WO | WO 9213068 A | 8/1992 |

OTHER PUBLICATIONS

Lee J. et al. (1996) Biotechnol. Bioengg. vol. 52:572–578.*
van Belkum MJ. (1991) J. bacteriol. vol. 173(24):7934–7941.*

Chandrapati, Sailaja et al., "Nisin independent induction of the nisA promoter in Lactococcus lactis during growth in lactose or galactose," FEMS Microbiology Letters, 170:(1):191–198 (1999).

Herman, R.E. et al., "Characterization of Plasmids and cloning of the β–Galactosidase Gene from Streptococcus-Thermophilus," Ferretti, J.J. and R. Curtiss, III (eds), Streptococcal Genetics, pp. 225–228 (1987) (Florida, USA, May 21–24, 1986. American Society for Microbiology: Washington, D.C. USA).

Champluvier et al., "Preparation of properties of β–galactosidase confined in cells of Kluyveromyces sp." Enzyme Microb. Technol., vol. 10, pp. 611–617 (1988).

Marteau et al. "Effect of the microbial lactase (EC 3.2.1.23) activity in yoghurt on the intestinal absorption of lactose: an in vivo study in lactase–deficient humans" British Journal of Nutrition, vol. 64, pp. 71–79 (1990).

Rao, "Oral supplements to improve lactose digestion and tolerance" Food Science and Technology International, vol. 3, pp. 87–92 (1997).

Ruyter et al., "Functional Analysis of Promoters in the Nisin Gene Cluster of *Lactococcus lactis*" Journal of Bacteriology, vol. 178, pp. 3434–3439 (1996).

Ryan, "Living with Lactose Intolerance" Today's Chemist at Work, pp. 49–52 (1998).

Somkuti et al., "Lactose Hydrolysis by Lactose Transport System Defective (lacS⁻) *Streptococcus thermophilus*" Biotechnology and Applied Biochemistry, vol. 12, pp. 351–356 (1990.).

Somkuti et al., "Permeabilization of *Streptococcus thermophilus* and the expression of beta–galactosidase" Enzyme Microb. Technol., vol. 16, pp. 573–576 (1994).

Somkuti et al., "Permeabilized *Streptococcus thermophilus* in the preparation of low–lactose milk" Biotechnol. Appl. Biochem., vol. 21, pp. 23–29 (1995).

Somkuti et al., "Sensitivity of *Streptococcus thermophilus* to Chemical Permeabilization" Current Microbiology, vol. 32, pp. 101–105 (1996).

Somkuti et al., "Permeabilization of *Streptococcus thermophilus* and *Lactobacillus delbrueckii* subsp. Bulgaricus with Ethanol" Current Microbiology, vol. 36, pp. 202–206 (1998).

Wang et al., "New Preparation for oral administration of digestive enzyme lactase complex microcapsules", Biomet. Art. Cells & Immob. Biotech., vol. 21, pp. 637–646 (1993).

* cited by examiner

*Primary Examiner*—Manjunath N. Rao
(74) *Attorney, Agent, or Firm*—Fish & Richardson P.C.

(57) ABSTRACT

The invention features methods and compositions for rapidly and effectively hydrolyzing lactose using recombinant lactic acid bacteria.

16 Claims, 12 Drawing Sheets

US 6,833,260 B1

LACTOSE HYDROLYSIS

This application claims benefit from previously filed Provisional Application No. 60/158,668, filed on Oct. 8, 1999, which is incorporated herein by reference in its entirety.

FIELD OF THE INVENTION

The present invention relates to the use of lactic acid bacteria to reduce lactose in dairy products and their use in food and other commercial applications.

BACKGROUND OF THE INVENTION

Lactose, or milk sugar, is a disaccharide carbohydrate that is hydrolyzed to glucose and galactose by the enzyme lactase, also known as beta-galactosidase (β-galactosidase). Although lactase is normally present in humans in intestinal epithelial cells and thereby contributes to the digestion of lactose present in dairy foods, a significant number of the adult human population is unable to digest lactose due to a genetic deficiency of this enzyme. Persons deficient in lactase may react to the consumption of dairy products with symptoms including nausea, cramps, gas, and diarrhea, a clinical condition known as lactose intolerance. Temporary lactase deficiencies in individuals with normal lactase levels may also result from damage to the intestinal lining produced by viral or bacterial infections, cancer chemotherapy, allergic or autoimmune conditions, and from decreases in lactase associated with aging. Persons who are lactase deficient and wish to consume normal dairy products with high lactose levels such as milk (12–13 grams of lactose per glass) can either purchase lactase treated dairy foods (70–100% hydrolyzed lactose) or consume a dietary supplement of lactase enzyme before each dairy meal. The cost and properties of current lactase preparations have limited the availability of lactose-reduced or free dairy products and other foods. Improvements in enzyme production costs and hydrolysis reaction properties could lead to the availability of a larger number of lactose reduced and free dairy foods and ingredients as well as more effective prophylactic products.

SUMMARY

The invention is based, in part, on the discovery of a method of achieving enhanced lactose hydrolysis using lactic acid bacteria. More specifically, the invention relates to a method of hydrolyzing lactose by using lactic acid bacteria that produce high levels of β-galactosidase, permeablizing the bacteria such that lactose can enter the cell and be hydrolyzed by the highly concentrated β-galactosidase contained therein. The above method results in the generation of permeablized lactic acid bacteria which contain high concentrations of β-galactosidase (referred to herein as lactase microcarriers) and which have a surprisingly high ability to rapidly and efficiently hydrolyze lactose under a variety of conditions. Moreover, the lactase microcarriers also have protease and bile resistant properties making them an ideal supplemental enzyme and oral prophylactic against the clinical condition of lactose intolerance.

Accordingly, the invention features a method for preparing a lactase microcarrier for hydrolyzing lactose in a liquid, e.g., milk, a whey product, or derivatives thereof. The method includes transforming a food-grade lactic acid bacterium with a DNA construct, wherein the DNA construct includes a promoter sequence of a gene operatively linked to a DNA sequence encoding a β-galactosidase, culturing the transformed bacterium under conditions that enable expression of the β-galactosidase such that the β-galactosidase activity exhibited in the bacterium is at least about 4000 MU (e.g., at least 4500, 5000, 6000, 7000, 8000, 9000, 10,000, 11,000 or 15,000 MU), and permeabilizing the bacterium. The method can further include contacting the permeabilized bacterium with a liquid containing lactose for a time sufficient to hydrolyze the lactose. The lactic acid bacterium can be a Streptococcus, Aerococcus, Carnobacterium, Enteroccus, Erysipelothrix, Gemella, Globicatella, Lactobacillus, Lactococcus, Bidobacteria, Leuconostoccocus, Pediococcus, Streptococcus, Tetragenococcus, or Bagococcus bacteria. In particular, the lactic acid bacterium can be a *Lactococcus lactis*. The DNA sequence encoding the β-galactosidase can be selected from the group *Streptococcus thermophilus, Lactobacillus bulgaricus, Bifobacterium species, Aspergillus niger, Aspergillus oryzae, Kluyveromyces fragilis, Kluyveromyces lactis, Bacillus subtillus* or Arthrobacter species. The promoter can be a promoter from a gene that encodes an antimicrobial peptide, e.g., a lantibiotic, e.g., a nisin gene promoter, such as a nisA promoter. The bacterium can be permeabilized by an agent such as a chemical, a solvent (e.g., ethanol or isopropanol), or a detergent, (e.g., deoxycholate, sodium dodecyl sulfate, rhamnolipid, or chenodeoxycholate). In one embodiment of the method, hydrolysis of lactose is performed at 4° C. In this embodiment, at least 90% of the lactose is hydrolyzed within 6 hours by a concentration of enzyme which is equivalent to 5000 o-nitrophenyl-β-galactosidase (ONPG) units/liter. In another embodiment of the method, hydrolysis of lactose is performed at 55° C. (or up to 63° C). In this embodiment, at least 90% of the lactose is hydrolyzed within 2 hours by a concentration of enzyme equivalent to 5000 ONPG units/liter.

In another aspect, the invention features a method for hydrolyzing lactose including providing a permeabilized lactic acid bacterium containing a β-galactosidase, wherein the bacterium exhibits a β-galactosidase activity of at least about 4000 Miller units, and contacting the permeabilized bacterium with a liquid containing lactose, for a time sufficient to hydrolyze the lactose. The lactic acid bacterium can be Streptococcus, Aerococcus, Carnobacterium, Enteroccus, Erysipelothrix, Gemella, Globicatella, Lactobacillus, Lactococcus, Bidobacteria, Leuconostoccocus, Pediococcus, Streptococcus, Tetragenococcus, or Bagococcus. In particular, the lactic acid bacterium is a *Lactococcus lactis*. The β-galactosidase can be encoded by a heterologous gene, e.g., a *Streptococcus thermophilus*β-galactosidase. In other embodiments, the bacterium exhibits a β-galactosidase activity of at least about 10,000 Miller Units.

In addition, the invention also features a permeabilized lactic acid bacterium containing a heterologous β-galactosidase, e.g., a *Streptococcus thermophilus* β-galactosidase, wherein the β-galactosidase exhibits an activity of at least about 4000 Miller Units. The permeabilized bacterium can be Streptococcus, Aerococcus, Carnobacterium, Enteroccus, Erysipelothrix, Gemella, Globicatella, Lactobacillus, Lactococcus, Bidobacteria, Leuconostoccocus, Pediococcus, Streptococcus, Tetragenococcus, or Bagococcus. In particular, the lactic acid bacterium can be a *Lactococcus lactis*. The permeabilized bacterium can be in a lyophilized form, in a concentrated cell suspension, or immobilized. In one embodiment, the invention includes a composition including the permeabilized bacterium containing a heterologous β-galactosidase which exhibits at least about 4000 Miller Units. In another embodiment, the invention includes a food product for use with a dairy product, wherein the food product includes the permeabilized bacterium containing a heterologous β-galactosidase which exhibits an activity of at least about 4000 Miller Units.

Also within the invention is a method of administering, e.g., orally, lactase to a mammal, the method including administering to the mammal the permeabilized bacterium containing a heterologous β-galactosidase which exhibits at least 4000 Miller Units.

The invention further features a reduced lactose dairy product including a dairy product, e.g., milk, and a permeablized *Lactococcus lactis*. The *Lactococcus lactis* can contain a *Streptococcus thermophilus* β-galactosidase.

"Food-grade bacteria" are microorganisms that are routinely consumed either as ingredients in fermented foods (e.g., cheese, bread, beer, yogurt) or as food or dietary supplements which aid in digestive processes (e.g. Lactobacilli, Bifidobacteria) and which have a record of being safe and non-toxic to consumers.

An "isolated nucleic acid" is a nucleic acid which has a non-naturally occurring sequence, or which has the sequence of part or all of a naturally occurring gene but is free of, or differentially positioned with respect to the genes that flank the naturally occurring gene of interest in the genome of the organism in which the gene of interest naturally occurs. The term therefore includes a recombinant DNA incorporated into a vector, into an autonomously replicating plasmid or virus, or into the genomic DNA of a prokaryote or eukaryote. It also includes a separate molecule such as a cDNA, a genomic fragment, a fragment produced by polymerase chain reaction (PCR), or a restriction fragment. It also includes a recombinant nucleotide sequence that is part of a hybrid gene, i.e., a gene encoding a fusion protein.

An "o-nitrophenyl-β-galactosidase unit (ONPG unit)" or "lactose unit (LU)" is a concentration of β-galactosidase which can hydrolyze a micromole of ONPG per minute, per liter of lactose containing liquid, e.g., milk or whey.

A first nucleic acid sequence that is "operably linked" to a second nucleic acid sequence is one that is incorporated into a genetic construct so that the first nucleic acid sequence, e.g., an expression control sequence, effectively controls expression of the second nucleic acid sequence, e.g., a gene encoding β-galactosidase.

A "polypeptide" or "protein" is any peptide-linked chain of amino acids, regardless of length or post-translational modification.

A "heterologous" nucleic acid sequence or protein is one that is not normally present in a given cell. For example, a gene such as LacZ from *Streptococcus thermophilus* (*St. thermophilus*), which is introduced into *Lactoccocus lactis* (*L. lactis*) is a heterologous LacZ in *L. lactis*.

A "conservative amino acid substitution" is one in which the amino acid residue is replaced with another residue having a chemically similar side chain. Families of amino acid residues having similar side chains have been defined in the art. These families include amino acids with basic side chains (e.g., lysine; arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

"Percent sequence identity" of two amino acid sequences or of two nucleic acid sequences is determined using the algorithm of Karlin and Altschul (*Proc. Natl. Acad. Sci. USA* 87:2264–2268, 1990), modified as in Karlin and Altschul (*Proc. Natl. Acad Sci. USA* 90:5873–5877, 1993). Such an algorithm is incorporated into the NBLAST and XBLAST programs of Altschul et al. (*J. Mol. Biol.* 215:403–410, 1990. BLAST nucleotide searches are performed with the NBLAST program, score=100, wordlength=12 to obtain nucleotide sequences homologous to a nucleic acid molecules of the invention. BLAST protein searches are performed with the XBLAST program, score=50, wordlength=3 to obtain amino acid sequences homologous to an aggregation-disposed polypeptide. To obtain gapped alignments for comparison purposes, Gapped BLAST is utilized as described in Altschul et al. (*Nucleic Acids Res.* 25:3389–3402, 1997). When utilizing BLAST and Gapped BLAST programs, the default parameters of the respective programs (e.g., XBLAST and NBLAST) are used. See http://www.ncbi.nlm.nih.gov.

Unless otherwise defined, all technical and scientific terms used herein have the same meaning as commonly understood by one of ordinary skill in the art to which this invention belongs. Although suitable methods and materials for the practice or testing of the present invention are described below, other methods and materials similar or equivalent to those described herein, which are well known in the art, can also be used. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

times the original cell density and the rate of lactose hydrolysis was measured in pasteurized skim milk.

Figure 7:
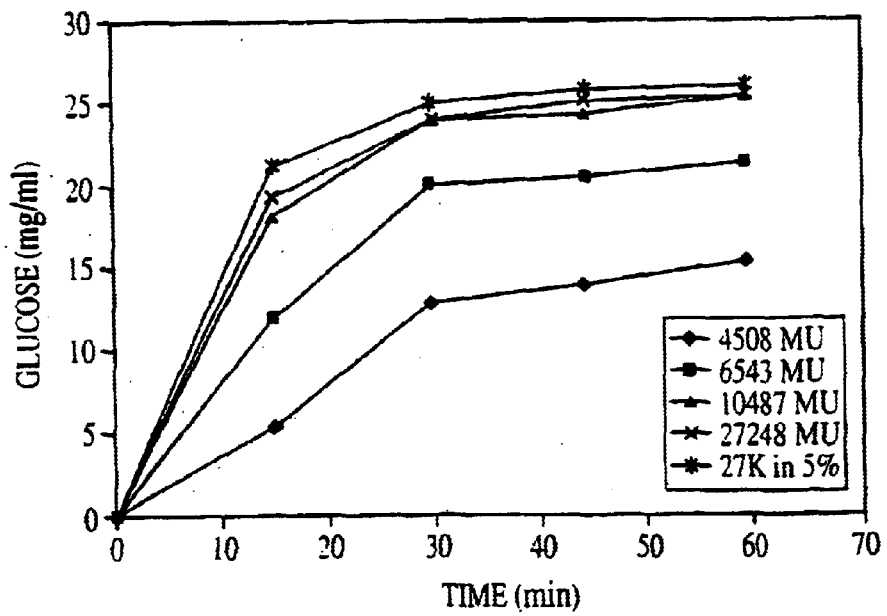

FIG. 7 is a line graph depicting the effect of microcarrier cells having various β-galactosidase activities on the rate of lactose hydrolysis in skim milk (4508 MU (circle), 6543 MU (solid square), 10487 MU (broken line), 27248 (fine x)), and in 5% lactose solution (27,000 MU (heavy x)) in *L. lactis* LM0230 (pDOC99; pDOC23).

Figure 8:
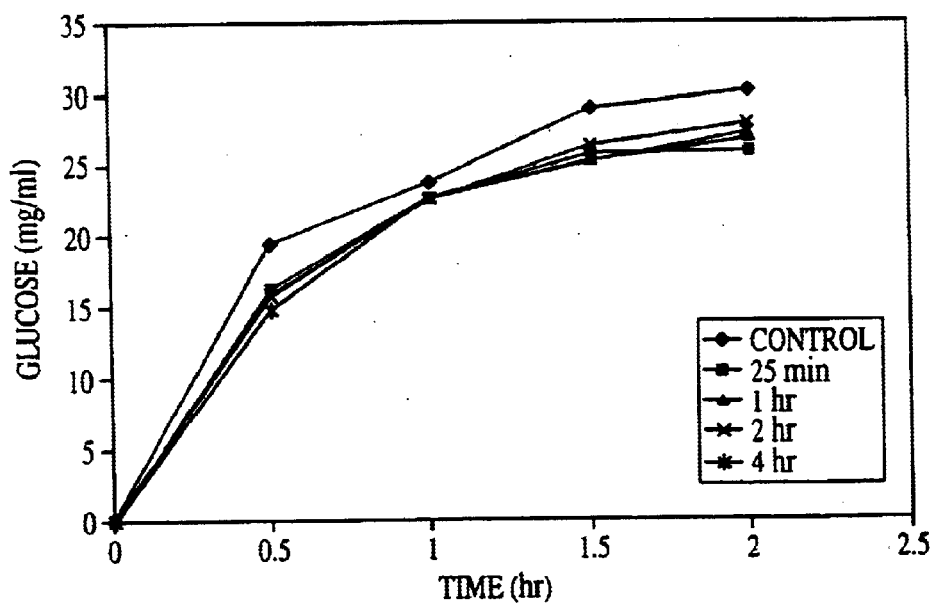

FIG. 8 is a line graph depicting the effect of increasing permeabilization time (0.5, 1, 1.5, and 2 hours) on the rate of *L. lactis* LM0230 (pDOC99; pDOC23) hydrolysis.

Figure 9:
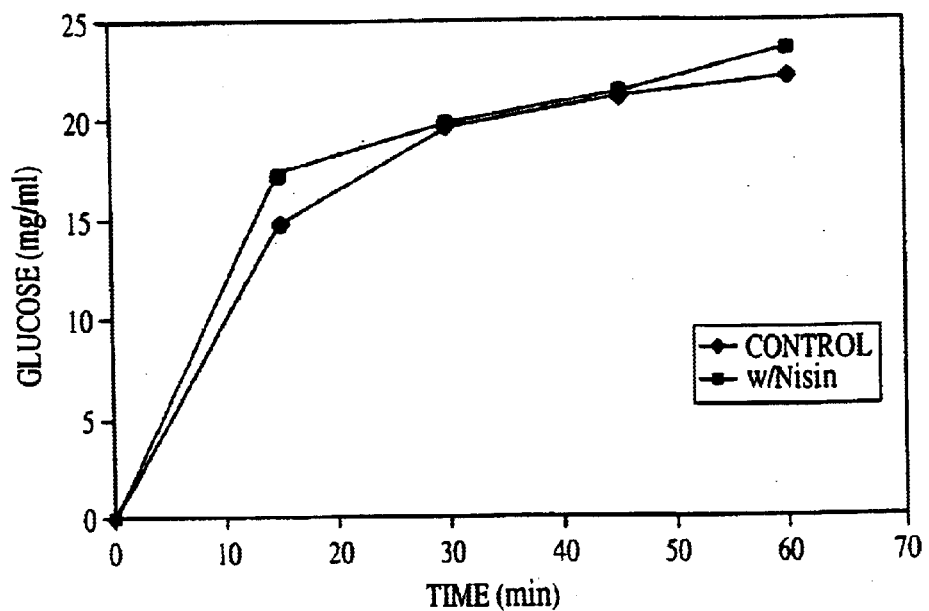

FIG. 9 is a line graph depicting the effect of permeabilization on the rate of hydrolysis over a one hour time period on cells exposed to 10 units nisin/ml (control cells, (diamond); nisin exposed cells (square shaped)).

Figure 10:
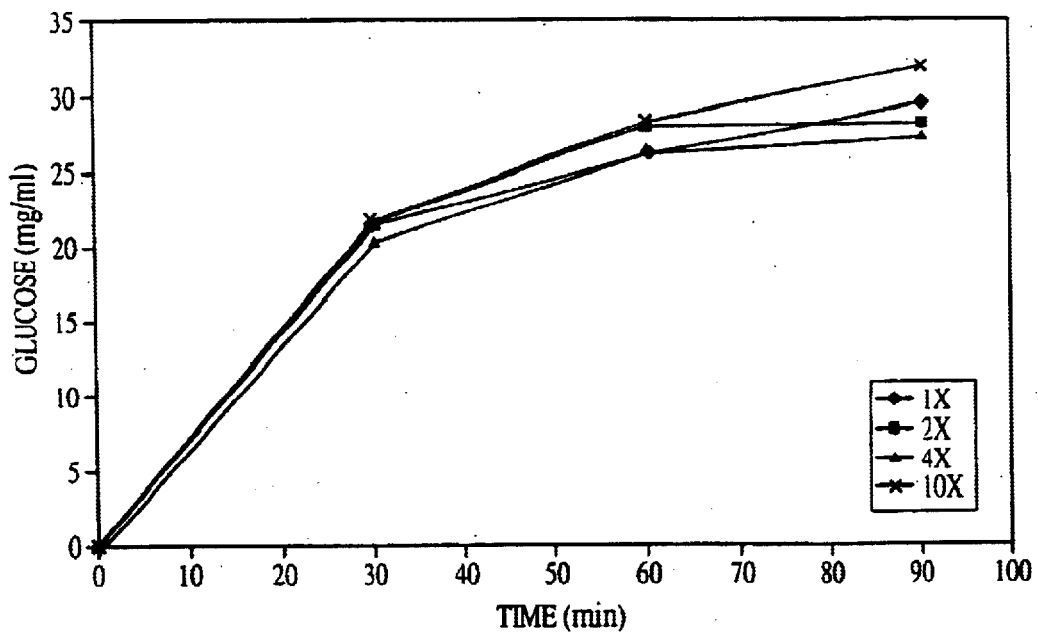

FIG. 10 is a line graph depicting the effect of 50% EtOH on the rate of hydrolysis over a one and one half hour time period on *L. lactis* LM0230 (pDOC99; pDOC23) cells, which are diluted once (circle), twice (square), four times (broken line), and 10 times (x).

Figure 11:
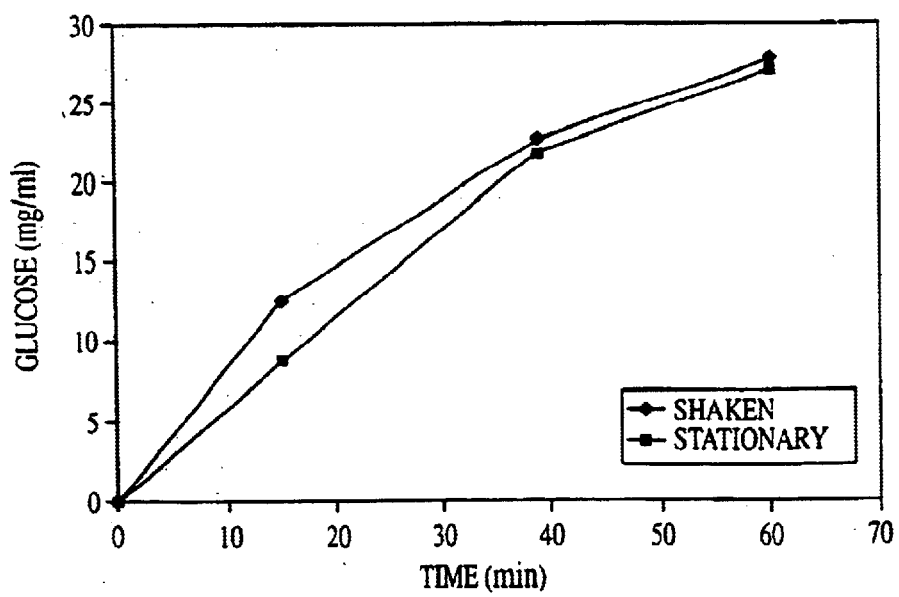

FIG. 11 is a graph depicting the rate of hydrolysis of lactose by permeabilized microcarrier cells which are shaken (circle) or not shaken (square).

Figure 12:
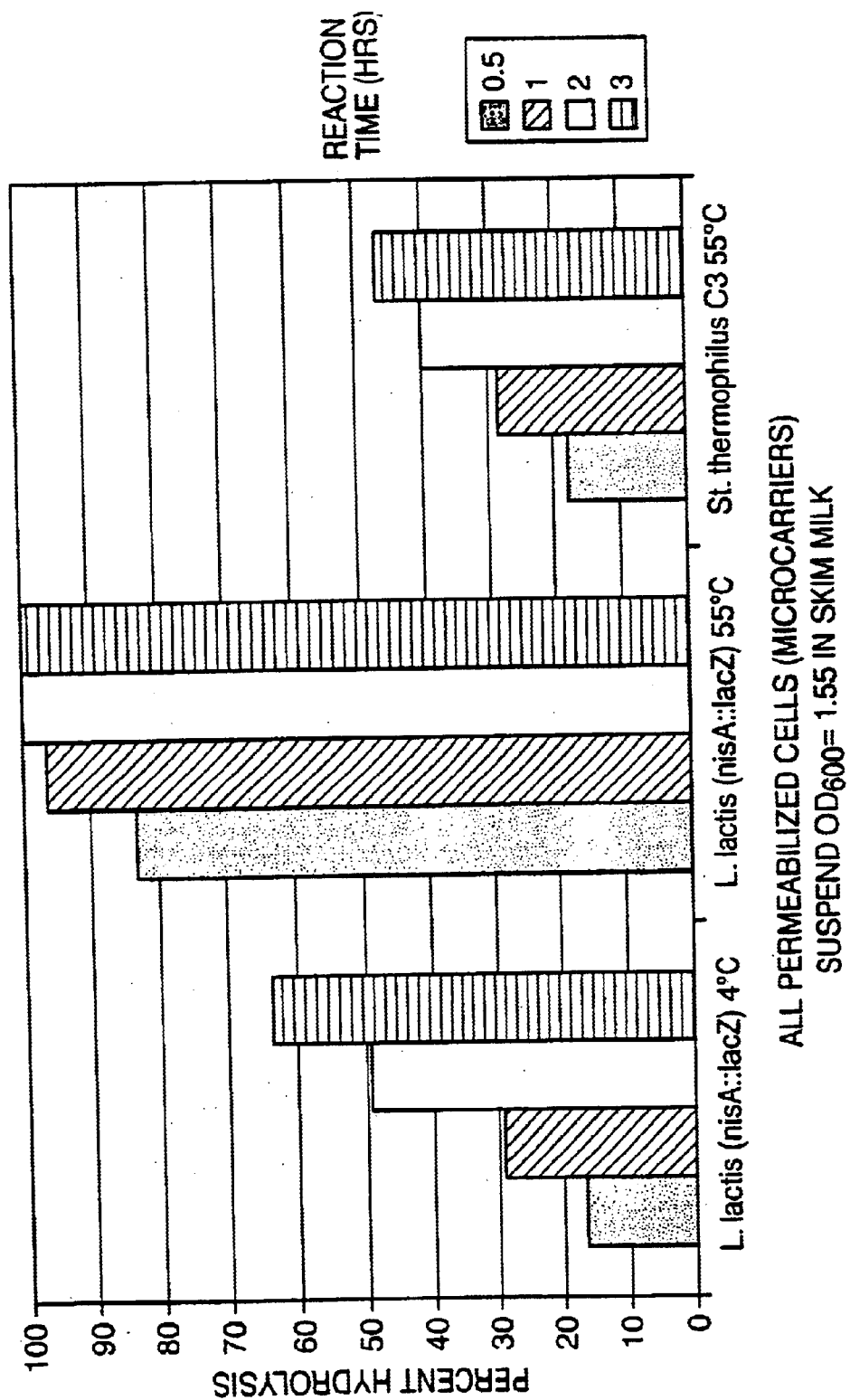

FIG. 12 is a histogram depicting a comparison of the percent lactose hydrolysis in skim milk of: (i) *L. lactis* (nisA::lacZ) microcarriers at 4° C.; (ii) *L. lactis* (nisA::lacZ) microcarriers at 55° C.; (iii) *St. thermophilus* C3 microcarriers at 55° C; over 0.5, 1, 2, and 3 hour reaction time period.

Figure 13:
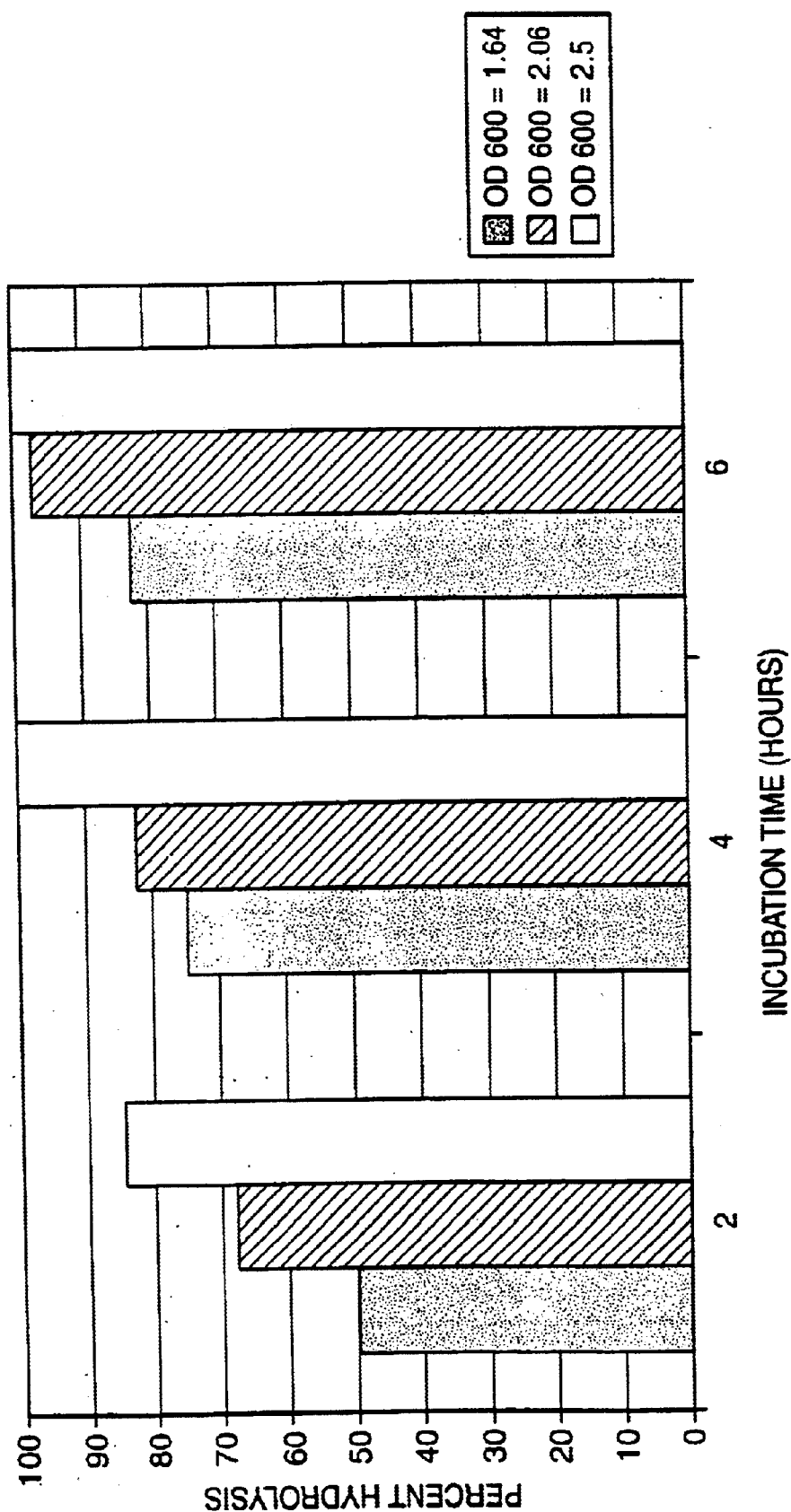

FIG. 13 is a histogram depicting the effects of varying *L. lactis* (nisA::lacZ) microcarrier concentration (i.e., $OD_{600}$ of 1.64 left bar), $OD_{600}$ of 2.06 (middle bar) and $OD_{600}$ of 2.5 (right bar)) on skim milk lactose hydrolysis at 4° C. over 2, 4, and 6 hour time periods.

Figure 14:
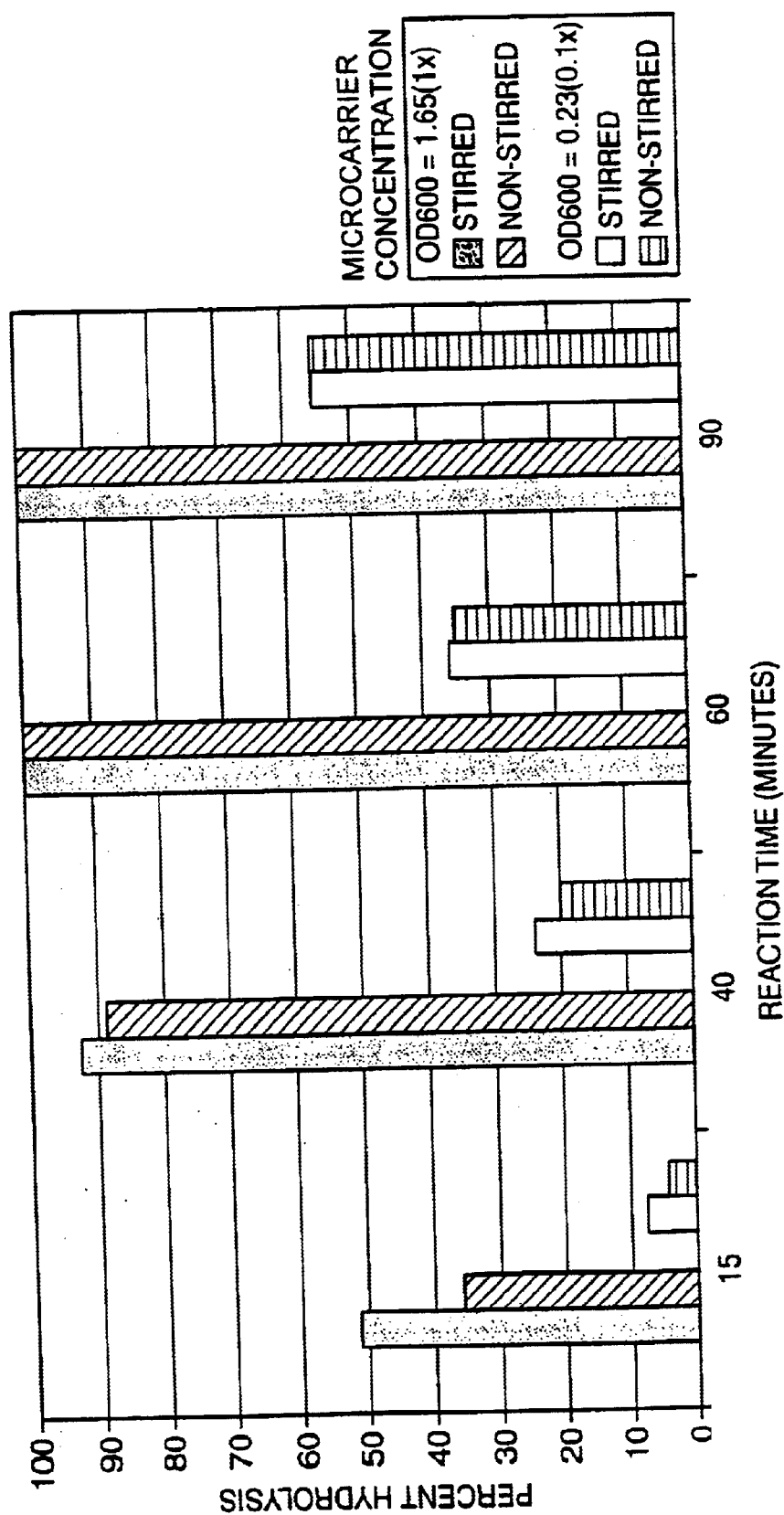

FIG. 14 is a histogram depicting the effects of stirring on milk lactose hydrolysis by lactase-microcarriers at different concentrations of $OD_{600}$=1.65(1×) (stirred (shaded bar) and not stirred (right bars); bars shown next to each other) and $OD_{600}$=0.23 (0.1×) (stirred (left) and not-stirred (right); bars shown next to each other) at 15, 40, 60, and 90 minutes.

Figure 15:
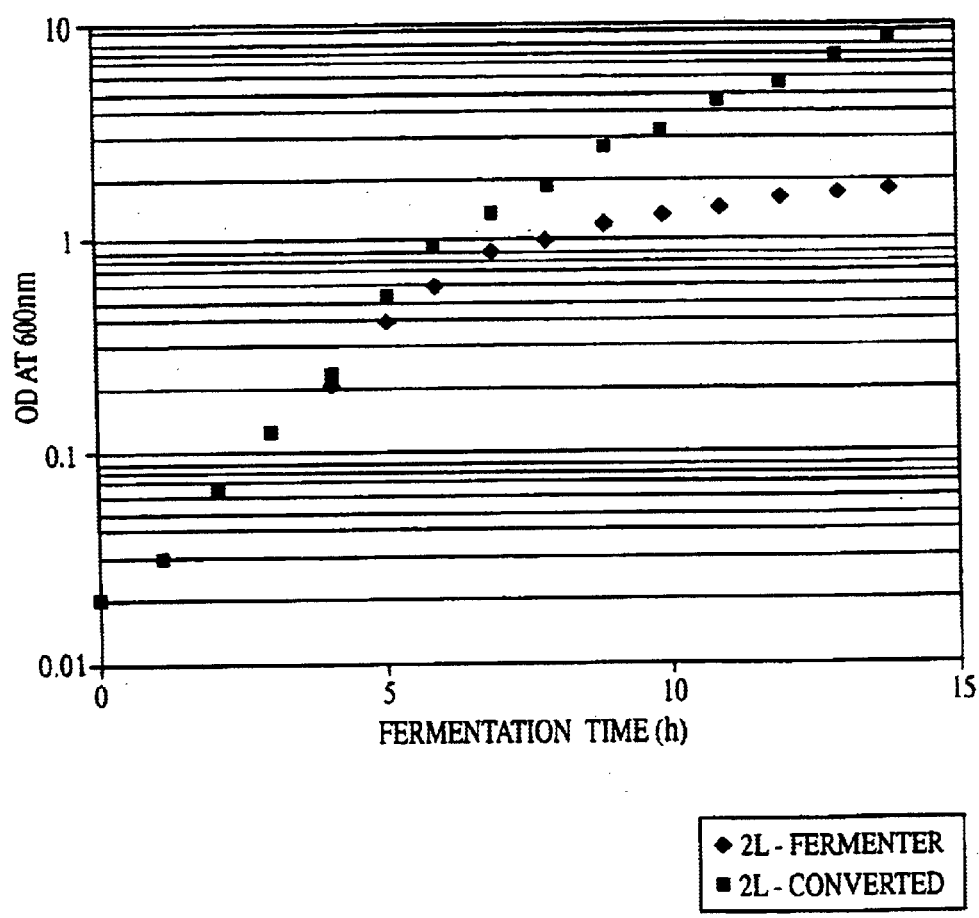

FIG. 15 is a line graph which depicts the growth of *L. lactis* NZ3900 in super MRS media.

Figure 16:
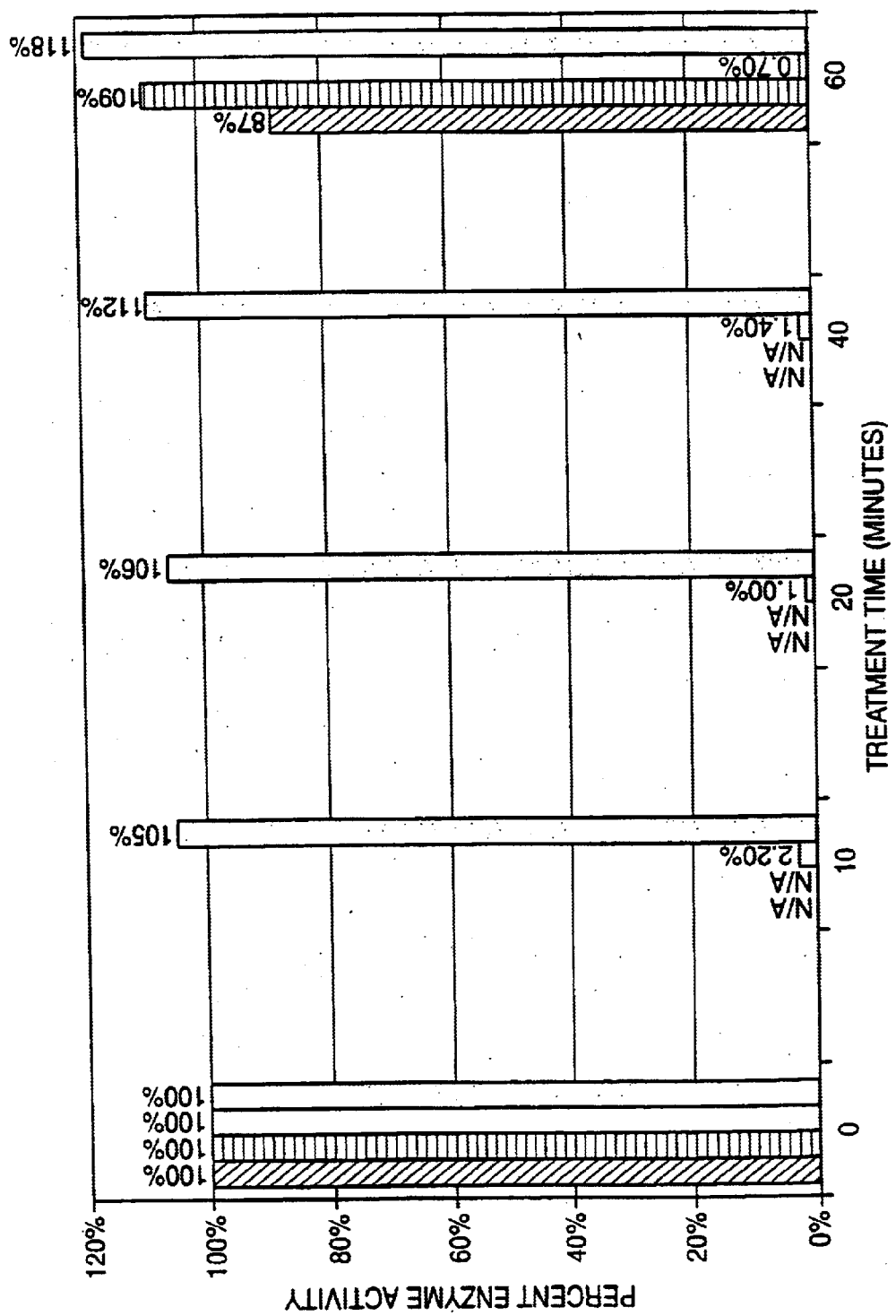

FIG. 16 is histogram depicting the effects of simulated intestinal fluid (Pancreatin pH 8.0; 37° C.) on enzymatic activities of yeast lactase (▨) and lactase microcarriers NZ3900 (■). Control enzymatic activities of yeast lactase (▨) and lactase microcarriers NZ3900 (▤) are also shown.

Figure 17:
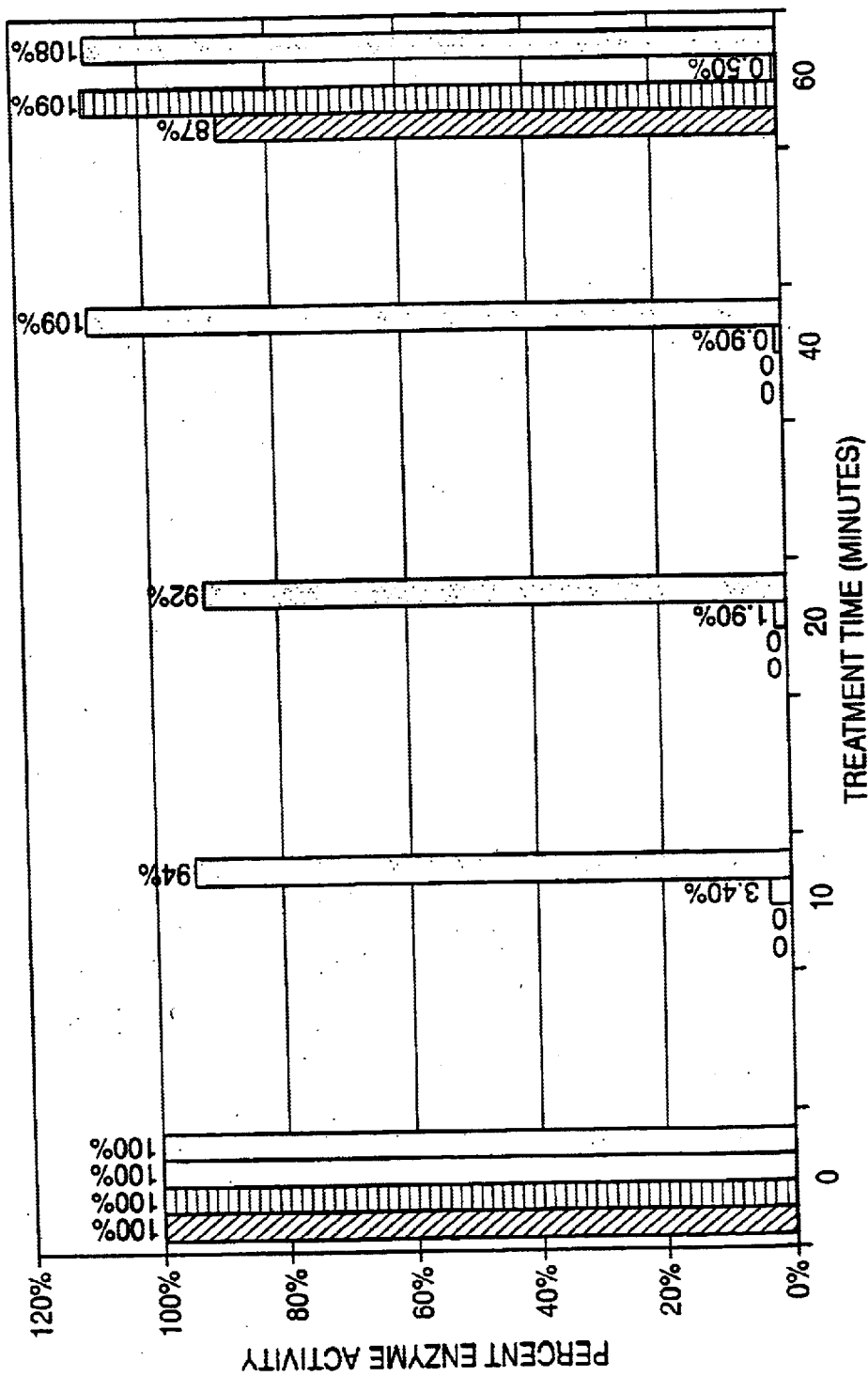

FIG. 17 is a histogram depicting the effects of simulated intestinal fluid (Pancreatin+0.1% bile, pH 8.0; 37° C.) on enzymatic activities of yeast lactase (▨) and lactase microcarriers NZ3900 (■). Control enzymatic activities of yeast lactase (▨) and lactase microcarriers NZ3900 (▤) are also shown.

DETAILED DESCRIPTION OF THE INVENTION

The invention is based, in part, on new lactase-containing microcarriers that have a surprising ability to rapidly hydrolyze lactose at both low and high temperatures. Specifically, these lactase-containing microcarriers contain high concentrations of β-galactosidase, e.g., β-galactosidase activity of at least about 4000 MU/permeabilized bacterium or microcarrier.

Lactic Acid Bacteria

The invention features lactic acid bacteria that express high levels of β-galactosidase or which have been manipulated to express heterologous β-galactosidase for the purposes of hydrolyzing lactose. Examples of useful lactic acid bacteria include Aerococcus, Carnobacterium, Enteroccus, Erysipelothrix, Gemella, Globicatella, Lactobacillus, Lactococcus, Bidobacteria, Leuconostoccocus, Pediococcus, Streptococcus, Tetragenococcus, and Bagococcus bacteria. In particular, the invention includes those lactic acid bacteria which are "food-grade" and, which have been accorded GRAS (Generally Regarded As Safe) status by the Food and Drug Administration. The term "food-grade" refers to those microorganisms which are routinely consumed either as ingredients in fermented foods (e.g., cheese, bread, beer, yogurt), or as food or dietary supplements, and have been found to be safe and non-toxic to the consumer. In particular, species of lactococcus, such as *L. lactis*, are useful in the invention.

β-Galactosidase/Lactase

"β-galactosidase" or "lactase" are used interchangeably by those in the art to refer to the same enzyme, which hydrolyzes lactose into its component monosaccharides glucose and galactose. The present invention features a method of hydrolyzing lactose using either: (i) lactic acid bacteria that produce a high concentration of active endogenous β-galactosidase, i.e., at least 4000 MU/bacterium; or (ii) lactic acid bacteria which have been manipulated to produce high concentrations of an analogous or a heterologous β-galactosidase, i.e., at least 4000 MU/bacterium.

Lactic acid bacteria can be manipulated to produce a high levels of active endogenous β-galactosidase by altering the expression control sequences of the endogenous β-galactosidase. The expression control sequences can be altered to enhance expression and production of β-galactosidase by any known method in the art. For example, chemical inducers such as such as ultraviolet light, nitrosylguanidine (NTG), and ethylmethylsulfanate (EMS) can be used to mutate the control sequences and enhance expression and production of β-galactosidase (see Experiments In Molecular Genetics, J. H. Miller, Cold Spring Harbor Press, Cold Spring Harbor, N.Y. 1977, pages 121–139).

Any heterologous β-galactosidase gene can be transformed into a lactic acid bacterium and used in the methods of the invention. β-galactosidase genes have been identified and characterized in prokaryotes and eukaryotes and the sequences are readily available in the art, e.g., in Genbank. Examples of known β-galactosidase genes which can be transformed into lactic acid bacteria include the β-galactosidase gene of *St. thermophilus* (Genbank accession# M63636), or human lactase (Genbank accession# NM002299). The β-galactosidase can be one which is active at high temperatures, such as those found in the β-galactosidase from *St. thermophilus, Bacillus stearothermophilia, Thermos aquaticos, Aspergillus niger, Aspergillus oryzae,* or one which is active at cold temperatures, such as *Bacillus subtillus* or the Arthrobacter species. Preferably, the β-galactosidase used is of food-grade, e.g., *Kluyveromyces fragilis,* or *Kluyveromyces lactis.*

In addition, functionally active variants of known β-galactosidases, (e.g., β-galactosidases which have conservative amino acid substitutions), can be used. For example, nucleic acid sequences which have at least 55% sequence identity to a known β-galactosidase, and nucleic acid sequences that hybridize to a known β-galactosidase can be transformed into a lactic acid bacterium and used in the method of the present invention, as long as they encode a protein that hydrolyzes lactose. Alternatively, β-galactosidase producing variants or mutants having higher levels of lactose hydrolysis activity than their wild-type counterparts can be used.

Expression Control Sequences and Vectors

To produce heterologous β-galactosidase in a lactic acid bacterium, a heterologous β-galactosidase gene (e.g., the *Streptoccus thermophilus*β-galactosidase gene) can be cloned into a vector such that it is operably linked to one or more expression control sequences. The expression control sequence can include one or more transcriptional promoters (such as a constitutive or inducible promoter), enhancers, suitable mRNA ribosomal binding sites, and sequences that terminate transcription and translation. Preferably, the promoter is an inducible promoter that strictly controls the expression of the β-galactosidase gene to which it is operably linked. When choosing a promoter, it is also preferable to choose a promoter that can be induced with a molecule whose presence is acceptable in a food product. Alternatively, a constitutive promoter that is always "on" can be used either with a heterologous gene or with an endogenous gene Examples of suitable expression control sequences include those of the antimicrobial peptides, such as the lantibiotics, e.g., nisin, subtilin, epidermin, gallidermin, salivarin, lucocin, pediocin, and lactiocin. Other expression control sequences that can be used for high level expression of lactase in lactic acid bacteria include the promoters for sucrose, phospho-β-galactosidase, and P32 temperate phage gene systems.

A non-limiting example of an appropriate expression regulatory sequence of an antimicrobial peptide for use in the present invention is a nisin gene promoter, such as nisin A (nisA) or nisin Z (nisZ) genes. The promoter of the nisA gene has been described previously by Buchman et al. (J. Biol. Chem. 263 (31), 16269–16266, 1988). The nisA promoter can be induced using nisin (autoregulated), or can be induced independent of nisin using lactose and galactose (Chandrapati et al., FEMS Microbiology letters, 170:191–198, 1999). In the case where activation of the promoter is induced by nisin, nisR and nisK are involved in the expression by the nisA promoter and therefore are required for nisin dependent activation of nisA.

Thus, to produce β-galactosidase under the control of a nisin promoter in a lactic acid bacterium, the nisA promoter sequence and the β-galactosidase gene can be cloned into a suitable expression vector and transformed, using any standard method (e.g., calcium chloride or electroporation), into an appropriate lactic acid bacterium that does not express nisin, e.g., *L. lactis* LM0230 and NZ3900. Since activation of the nisA promoter by nisin requires intact nisR and nisK genes, nisR and nisK must be present in the bacterium, e.g., the expression vector which contains the β-galactosidase gene can also contain nisR and nisK, or another expression vector which contains nisR and nisK is co-transformed into the bacterium, or nisR and nisK is introduced into the chromosome of the bacterium. The bacterium is then cultured under suitable conditions until an appropriate cell density is reached (e.g., OD600 of 0.7–1.4) and nisin is then added. The addition of nisin, and/or a suitable analogue/ derivative of nisin, to the culture medium is detected by the nisRK system and this signals the nisA promoter to induce expression of the β-galactosidase. Suitable culture media include whey based media, or milk.

The use of nisin as an inducer molecule is advantageous as nisin has food-grade status and its presence is acceptable in foodstuffs, e.g., dairy products.

Alternatively, a heterologous β-galactosidase gene can be incorporated into the genome of the host cell. For example, the β-galactosidase gene can be integrated into the chromosome of a lactic acid bacterium, e.g., downstream of the nisA promoter, using well-known chromosomal integration techniques.

Standard methods can be used by the skilled person to construct an appropriate expression vector for use in the present invention. See, generally, Sambrook et al., 1989, *Cloning—A Laboratory Manual* (2nd Edition), Cold Spring Harbor Press. Vectors useful in this invention include plasmid vectors and viral vectors.

β-Galactosidase Measurements

To determine the activity of the β-galactosidase produced in a lactic acid bacterium, a β-galactosidase activity assay can be performed using the o-nitrophenyl-β-galactosidase (ONPG) assay described by Miller et al. (Experiments in Molecular Genetics, Cold Spring Harbor Laboratory, Cold Spring Harbor, N.Y., 1972). Briefly, the β-galactosidase activity in a cell is monitored by first permeabilizing the cell, adding ONPG, allowing the reaction to proceed, and stopping the reaction. The Miller activity in Miller Units (MU) is calculated as follows:

$$MU = \frac{1000 \times (OD_{420} - (1.75 \times OD_{550}))}{T \times V \times OD_{600}}$$

where T=time (in minutes) for development of yellow color; V=volume (in ml) if

Alternatively, β-galactosidase activity can be expressed in ONPG units (μmoles of ONPG hydrolyzed per minute at 28° C.). ONPG units can be measured using the following equation:

ONPG Units=$OD_{420}$/min×21,300 ml/mmoles.

In this equation, 21,300 is the ONPG molar extinction coefficient.

In the methods of the present invention, the lactic acid bacteria, e.g., harboring the fusion of an inducible promoter operably linked to the β-galactosidase gene, are grown until an $OD_{600}$ of 0.8–1.2 is reached. The cells are then induced with an appropriate inducer molecule. The ability to measure β-galactosidase activity allows one skilled in the art to determine, e.g., the optimal amount of an inducer molecule that should be added to the bacterial culture so as to produce high levels of β-galactosidase. A lactic acid bacterium included in the invention produces at least about 4000 Miller Units (MU) of β-galactosidase per cell. For example, a culture of recombinant lactic acid bacteria as generated herein, in a volume of 1 ml, cultured until they reach an $OD_{600}$ of 1.2, induced with nisin (1.0 units/ml) will provide greater than about 4000 MU of β-galactosidase activity Permeabilization The lactic acid bacterial cells described herein that express and produce β-galactosidase are removed from the growth media and permeabilized. "Permeabilization" refers to a process whereby the cell membranes of the lactic acid bacteria are disrupted to allow the free passage of In lactose to the cell interior while allowing the retention of β-galactosidase in the cytoplasm of the cell. These permeabilized cells are also referred to as "microcarriers". Since the endogenous β-galactosidase is retained by permeablized cells, the treated bacteria can be directly used for hydrolyzing lactose in liquids such as milk Also, the advantage of permeabilizing the cells is that the permeabilization procedure renders the cells non-viable and inactivates other enzymes such as peptides and lipases that could contribute to the off-flavor in milk.

The membranes of the lactic acid bacteria can be permeabilized by physical methods such as sonication, or by chemicals such as organic detergents or solvents. Examples of detergents include deoxycholate, TRITONS®-X-100 (a non-ionic surface active detergent), OXGALL®, sodium dodecyl sulfate, and chenodeoxycholte. In particular, rhamnolipid can be used to disrupt cell membranes. Examples of useful solvents include ethanol or isopropanol. Since residues of the chemicals or detergents can remain associated with the treated cell, it is preferable that the chemical or detergent be non-toxic, and most preferably, food-grade. For example, since ethanol is present in trace amounts in many fermented dairy foods consumed by humans, its use is preferred for permeabilizing the cells.

Hydrolysis of Lactose by Perneabilized Lactic Acid Bacteria

To determine the extent to which the permeabilized lactic acid bacteria can hydrolyze lactose, the rate of lactose hydrolysis can be determined by measuring the increase in glucose concentration using commercially available kits such as glucose hexokinase kits (Sigma, St. Louis, Mo.). The present invention features a method of producing permeabilized lactic acid bacteria which have high levels of β-galactosidase activity. For example, bacteria produced by the methods of the invention have a β-galactosidase activity of between 4,000 and 30,000 Miller units. These bacteria show a high ability to rapidly hydrolyze lactose in liquids such as milk or whey over an expanded range of effective operating temperatures, i.e., at both high (e.g., 55° C.) and low (e.g., 4° C.) temperatures. For example, *L. lactis* microcarriers containing β-galactosidase from *St. thermophilus* were found to completely hydrolyze lactose in skim milk in less than one hour when suspended in the milk and incubated at 55° C. Complete lactose hydrolysis was also achieved at 4° C. in less than 8 hours.

To generate a lactic acid bacterium of the invention, optimal growth conditions, induction conditions, and cell density of the lactic acid bacterium of interest can be easily determined using the techniques and assays described herein.

Uses of the Permeabilized Lactic Acid Bacteria/Microcarriers

At The microcarriers described herein can be used as food and dietary supplements. For example, the microcarriers can be administered to a mammal such as a human, who is lactose intolerant. In this example, the microcarriers are administered before, or with, a dairy meal as a means of preventing the discomforting symptoms of lactose intolerance (gas, cramps, or diarrhea). The microcarriers can be administered alone or in a mixture, e.g., in the presence of a pharmaceutically acceptable excipient or carrier (e.g., physiological saline). The excipient or carrier is selected on the basis of the mode and route of administration. Suitable pharmaceutical carriers, as well as pharmaceutical necessities for use in pharmaceutical formulations, are described in *Remington's Pharmaceutical Sciences* (E. W. Martin), a well known reference text in this field, and in the USP/NF (United States Pharmacopeia and the National Formularly). For example, suitable liquid forms of the microcarriers can be prepared by incorporating the microcarriers in aqueous or non-aqueous dispersion, suspensions, or solutions with conventional liquid carriers, such as, for example, glycerol, edible glycols, and edible oils. A pharmaceutical composition is formulated to be compatible with its intended route of administration. Examples of routes of administration include oral, rectal, and enterally. Preferably, the microcarriers are administered orally.

Microcarriers that are administered orally generally include an inert diluent or an edible carrier. For the purpose of oral therapeutic administration, the microcarriers can be incorporated with excipients and used in the form of tablets, or capsules, e.g., gelatin capsules. Pharmaceutically compatible binding agents, and/or adjuvant materials can be included as part of the composition. The tablets, pills, capsules, and the like, can contain any of the following ingredients, or compounds of a similar nature: a binder such as microcrystalline cellulose, gum tragacanths or gelatin; an excipient such as starch or lactose, a disintegrating agent such as alginic acid, Primogel®, or corn starch; a lubricant such as magnesium stearate or Sterotes®; a glidant such as colloidal silicon dioxide; a sweetening agent such as sucrose or saccharin; or a flavoring agent such as peppermint, methyl salicylate, or orange flavoring.

In one embodiment, the microcarriers are coated with an enteric coating. The coating inhibits entry of materials into the microcarriers in the low pH environment of the stomach, e.g., at a pH of less than 4, but is dissolved or degraded and therefore enables entry of matierals (such as lactose) into the microcarriers in higher pH environments such as in the intestines, e.g., at a pH of about 5.5, or greater. Other coatings to delay activity of the microcarriers can also be used. Suitable materials for enteric and other coatings include, for example, hydroxypropyl methyl cellulose phthalate, hydroxypropylmethyl cellulose acetate succinate, hydroxypropyl methyl cellulose phthalate, hydroxypropyl methyl cellulose hexahydrophthalate, shellac, cellulose acetate, cellulose acetate phthalate, polyvinyl acetate phthalate, carboxymethyl ethyl cellulose, methacrylic acid copolymers, and methacrylic ester copolymers. For example, a commercially available enteric coating system (Sureteric YAE-6-18107®), which contains polyvinyl acetate phthalate, talc, polyethylene glycol, titanium dioxide, sodium bicarbonate, triethyl citrate, purified stearic acid, sodium alginate, and colloidal silicon dioxide, may be used.

The microcarriers described herein can also be added to a liquid containing lactose (e.g., a dairy product) in an amount suitable to hydrolyze the lactose so as to generate a lactose free or lactose reduced liquid. For example, the microcarriers of the invention can be used to hydrolyze lactose present in milk. The microcarriers can be added to milk prior to pasteurization or after pasteurization, as long as the microcarriers are not pasteurized prior to hydrolysing the lactose in the liquid.

To alleviate the need for a lactase intolerant individual to separately ingest a lactase enzyme preparation, the microcarriers described herein can be incorporated into a food product. For example, a commercially made food product can be manufactured to include microcarriers. The food product need not be a dairy food product, but can be a food product that is ingested in conjunction with a dairy food product. For example, the microcarriers can be coated onto a cereal product or included in a chocolate powder for use in milk. In another example, the microcarrier can be coated onto an ice cream cone, or combined with an ice cream bar coating.

The microcarriers can be immobilized, e.g., retained on a membrane, included in a gel or capsule, eg., in a calcium alginate gel. The advantage of immobilizing the microcarriers is that the microcarriers can be easily recovered and reused.

In addition, the microcarriers of the invention can be lyophilized and potentially stored for one, two, or more years at temperatures below freezing, e.g., at a temperature at or below−20° C.

Other methods of employing the microcarriers of the invention will be apparent to those skilled in the art

EXAMPLES

The invention is further illustrated by the following examples. The examples are provided for illustration only and are not to be construed as limiting the scope or content of the invention.

Example 1

Induction of β-galactosidase

*L. lactis* LM0230(pDOC23:pDOC99) was inoculated into 10 ml M17 plus 0.5% glucose, chloramphenicol (Cm) 3 μg/ml and erythromycin (Erm) 3 μg/ml, from a frozen stock maintained at −70° C., and incubated at 30° C. in a dry incubator overnight. For production of β-galactosidase a volume of M17 broth plus 0.5% glucose; Cm, 3 μg/ml; and Erm, 3 μg/ml; (generally between 50 and 200 ml) was inoculated 5% from the overnight culture and incubated at 30° C. in a water bath. After attaining an $OD_{600}$ between 0.6 and 1.2 the culture was induced with nisin to a final concentration of 1.0 IU/ml by adding 1.0% of a 100 IU/ml stock solution. The stock solution was prepared by suspending 0.0083 g PERLAC™ per ml in 0.02 N HCl+1.0% TWEEN™ 80.

β-Galactosidase Activity Assay

β-galactosidase activity was monitored during the induction period using the Miller assay (2) by the following procedure. 1 ml of culture was removed and the $OD_{600}$ recorded in a DU 70 spectrophotometer. 100 μl of this sample was added to 0.9 ml of LacZ buffer (60 mM $Na_2HPO_4.7H_2O$, 40 mM $NaH_2PO_4.H_2O$, 10 mM KCl, 1 mM $MgSO_4.7H_2O$,), 20 μl of chloroform added and incubated at 37° C. with shaking (225 rpm) to permeabilize the cell membrane. Activity was determined by adding 200 μl of ONPG (4 mg/ml prepared in $HPO_4$ buffer: 3.48 g $H_2PO_4.H_2O$, 3.85 g $Na_2HPO_4$ in 100 ml $dH_2O$). After development of sufficient yellow color, the reaction was stopped by adding 500 μl of a 1 M $Na_2CO_3$ solution. The exact time for the reaction was recorded in minutes for use in the Miller unit activity calculation. A control was prepared by adding 100 μl of sterile media to 900 μl of LacZ and processing along with the test samples. The control was incubated with ONPG for 60 minutes before stopping the reaction with 1M $Na_2CO_3$.

Following the reaction, the samples were centrifuged for 5 minutes at RT and the supernatant removed for recording the optical density at both 420 and 550 nm. The Miller activity was calculated as described above.

Figure 1:
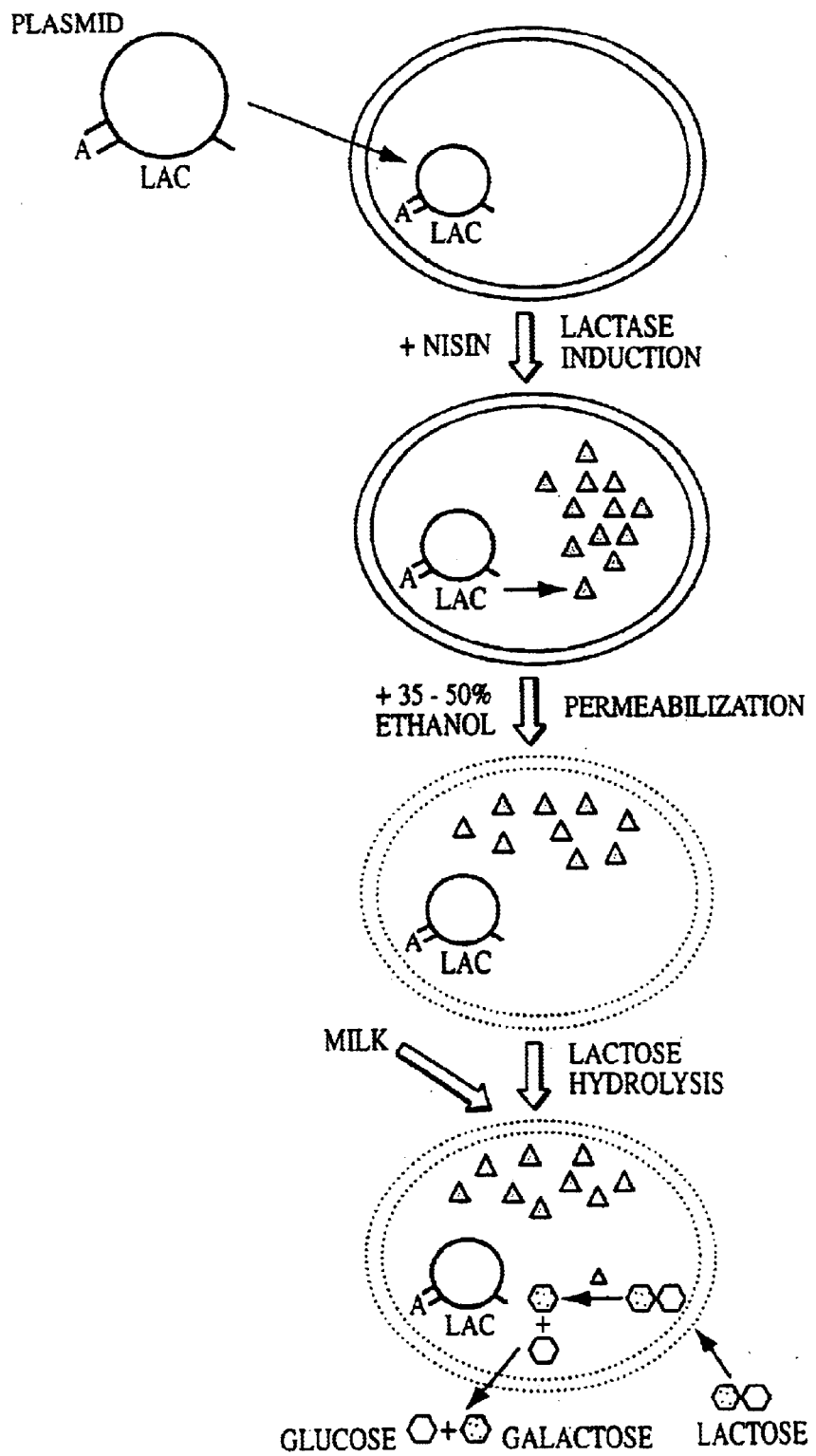
FIG. 1 is a schematic diagram depicting the production of lactase microcarriers and their use in milk lactose hydrolysis.
Figure 2:
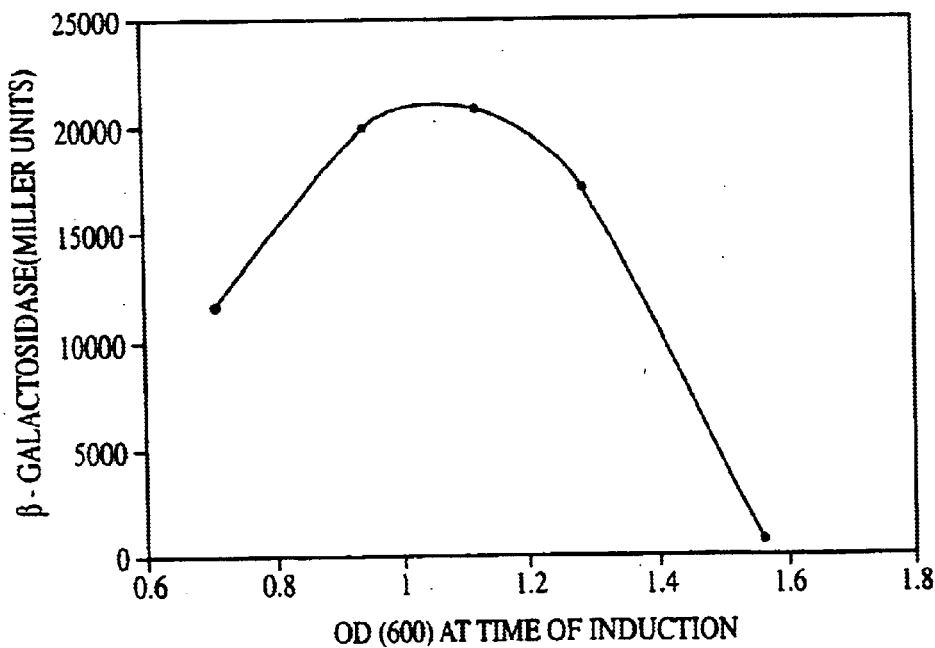
FIG. 2 is a line graph showing β-galactosidase activity of *L. lactis LM0230* (pDOC99;pDOC23) induced at $OD_{600}$ of 0.7 with 1.0 unit/ml nisin and incubated at 30° C.

The maximum activity of LM0230 (pDOC23:pDOC99) cells grown in M17G and induced with nisin consistently occurred approximately 2.5 hours after induction. Increased incubation beyond 2.5 hours resulted in a gradual decrease in Miller unit activity (FIG. 2).

Figure 3:
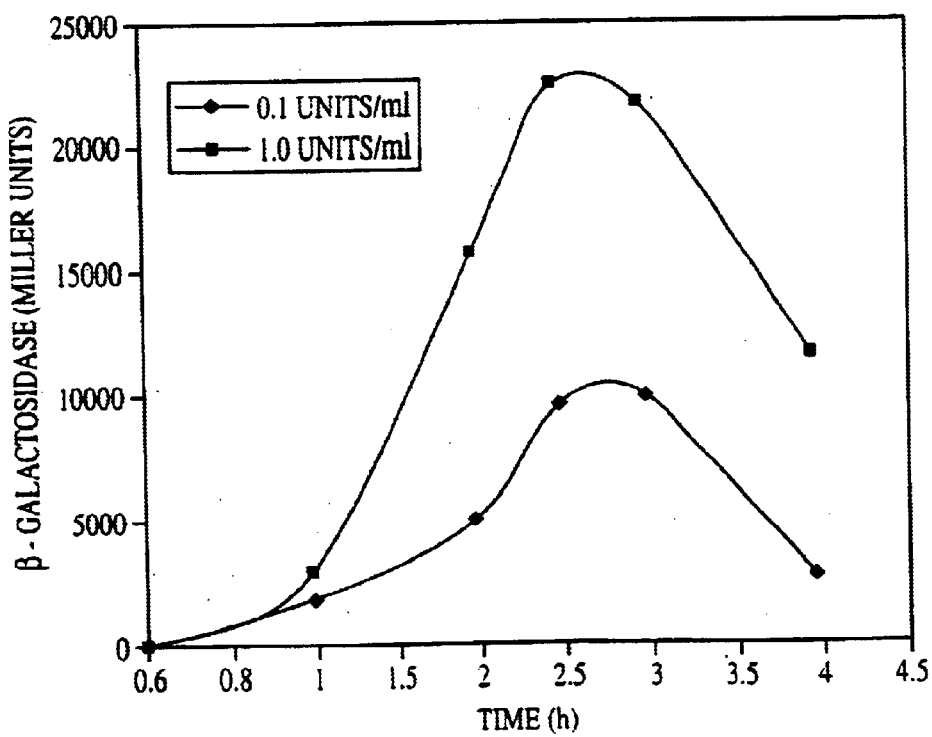
FIG. 3 is a line graph showing β-galactosidase activity of *L. lactis* LM0230 (pDOC99;pDOC23) induced with 1.0 unit/ml nisin (square box) and 0.1 units/ml nisin (diamond box).

The activity of induced cells was proportional to the concentration of nisin added up to a level of approximately 1.0 units/ml (FIG. 3). Above. 1.0 units/ml, cell growth was attenuated and activity levels were subsequently decreased.

Figure 4:
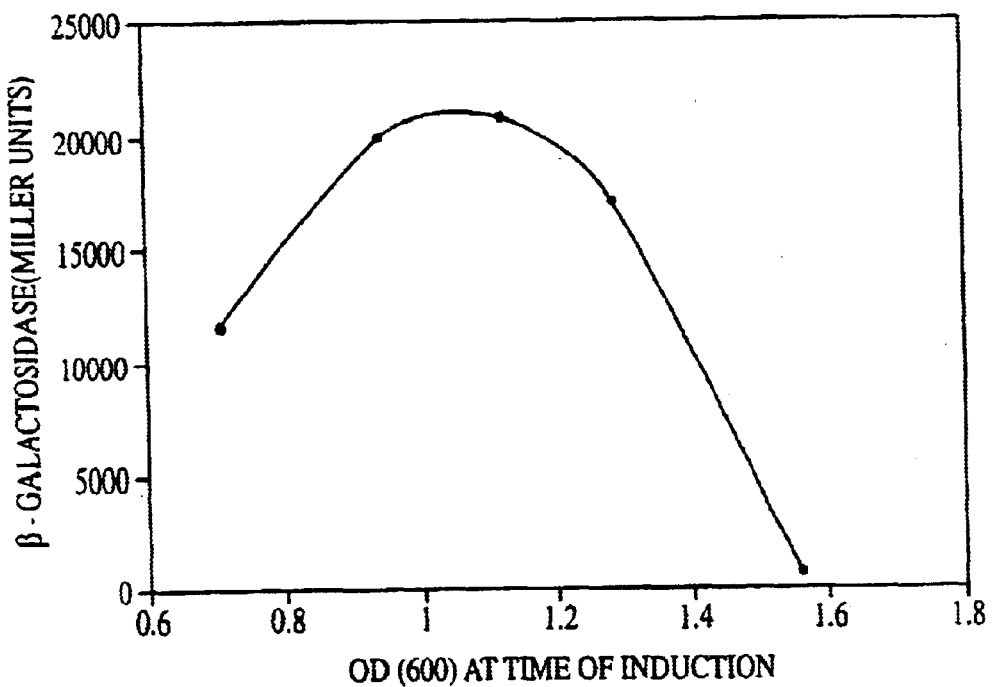
FIG. 4 is a line graph of β-galactosidase activity maximums of *L. lactis* LM0230 (pDOC99;pDOC23) cultures induced at various $OD_{600}$ with 1.0 units/ml nisin. Each culture was induced and incubated for 2.5 hours before measuring activity.

The optimum cell density for induction was determined by inducing cultures at various cell densities and comparing maximum levels of β-galactosidase activities. The optimum activity was observed when cultures were induced at an $OD_{600}$ of approximately 1.0 to 1.2 (FIG. 4).

Example 2

Permeabilization of Cells to Facilitate Lactose Hydrolysis

General Method of Permeabilization of Cells

Following induction of the lacZ gene, the cells were removed from the growth media and permeabilized to facilitate transport of lactose, preserve the activity of the enzyme, and render the cells non-viable. The cells were centrifuged at 10K rpm in a Beckman JA-20 rotor for 15 minutes at 4° C. in a Beckman J2-21 centrifuge and washed once in ice cold distilled water. The cells were pelleted again and resuspended with 0.5×volume of POM buffer (50 mM $K_2HPO_4$, 50 mM $KH_2PO_4$, 1 mM $MgCl_2$, pH 7.4). Permeabilization was accomplished by adding 0.5×volume of 100% EtOH for a final concentration of 50% EtOH, and incubating at room temperature for 25 minutes. The cells were then pelleted, washed once with ice-cold POM buffer, and resuspended to the original culture volume in POM buffer. The cells were then stored at 4° C. until required for lactose hydrolysis.

Example 3

Hydrolysis of Lactose by Permeabilized LM0230 (pDOC23:pDOC99) Cells

General Method of Lactose Hydrolysis

Following permeabilization and resuspension of the cells in POM buffer, they could be used for lactose hydrolysis, acting as "enzyme microcarriers". This hydrolysis was tested both in a 5% lactose solution as well as in pasteurized milk according to the following general method. A volume of stored cells was pelleted by centrifugation, the supernatant was removed, and the cells were resuspended in an equal volume of the 5% lactose solution or pasteurized milk. The suspension was then incubated, and lactose hydrolysis was monitored by measuring the increase in glucose concentration using Sigma Glucose Hexokinase (HK) kits.

Glucose Hexokinase Assay

In the glucose assay, the glucose is first phosphorylated in a reaction catalyzed by the, hexokinase. Glucose-6-phosphate is formed and then oxidized to 6-phosphogluconate in the presence of $NAD^+$, a reaction catalyzed by glucose-6phosphate dehydrogenase. During this oxidation, the $NAD^+$ is reduced to NADH, the concentration of which is directly proportional to the glucose concentration. The absorbance of NADH at 340 nm is then a direct correlation of the glucose concentration.

A standard curve of glucose concentration was prepared from stock solutions of 5% lactose, and 2.5% glucose/2.5% galactose. Because the absorbance at 340 nm of a 2.5% glucose solution (the theoretical concentration due to complete hydrolysis of 5% lactose) is beyond the linear range of the glucose HK kit, each standard was diluted 1:4 by adding 25 μl of standard to 75 μl $sdH_2O$. Ten μl of the diluted standard was then added to 1.0 ml of the HK reagent and incubated at 37° C. for five minutes. Absorbance at 340 nm was recorded and the standard curve prepared.

For determination of glucose in the samples during incubation with the microcarriers 100 μl was removed to a 1.5 ml microcentrifuge tube and centrifuged at max speed for ten minutes to pellet the cells and milk proteins which could interfere with the absorbance readings of the glucose. HK assay. For the assay, 25 μl was removed from the top of the liquid sample and diluted with 75 μl of $sdH_2O$. Ten μl of this diluted sample was added to 1.0 ml of the glucose HK reagent and incubated at 37° C. for 5 minutes. Absorbance readings were taken at 340 nm, measured against the standard curve, and values given in mg/ml glucose. A control was prepared by adding 10 μl of a diluted sample to 1.0 ml of 0.85% saline to determine the absorbance error due to the turbidity of the samples. In all cases, this was determined to be negligible. The expected maximum level of glucose, based on 5.0% lactose in milk, is approximately 25 mg/ml.

Effect of Temperature on Rate of Lactose Hydrolysis

Figure 5:
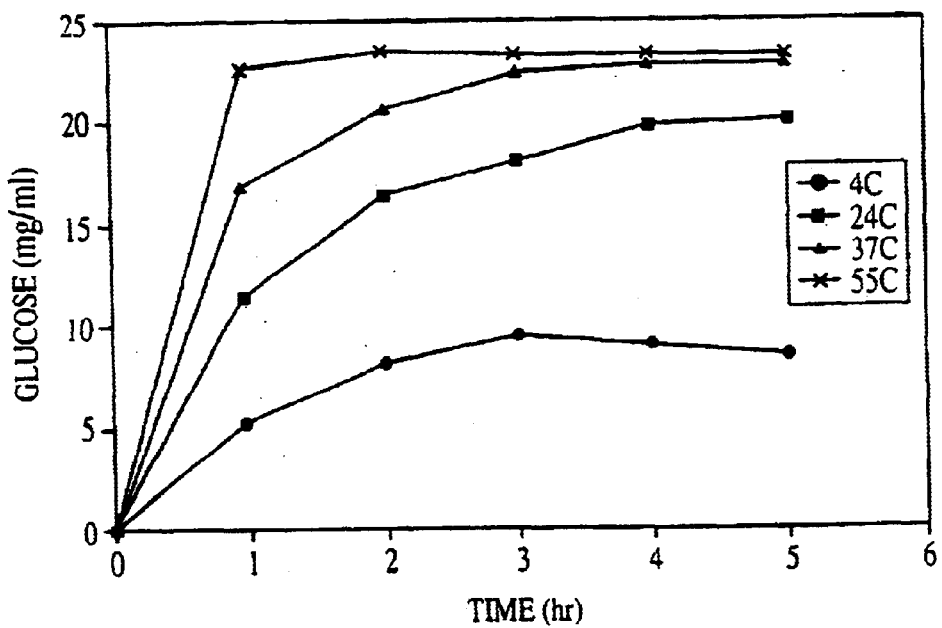
FIG. 5 is a line graph depicting the effect of a range of different temperature (4° C. (diamond shape), 24° C. (square box), 37° C. (triangle shaped) and 55° C. (x shaped) on the rate of lactose hydrolysis of a *L. lactis* LM0230 (pDOC99;pDOC23) culture. The rate of lactose hydrolysis is indirectly measured as the increase in glucose concentration.

The effect of temperature on the rate of lactose hydrolysis was tested by incubation of the suspended microcarriers in pasteurized skim milk at 4, 24, 37, and 55° C. (FIG. 5).

While activity was observed throughout this temperature range, incubation at 55° C. was found to result in the highest rate of lactose hydrolysis.

During incubation at 4° C. the suspended cells settled to the bottom of the tube, which may explain why the amount of lactose hydrolyzed leveled off well below the theoretical maximum. A repeat of this incubation with constant agitation of the cell suspension revealed that maximum hydrolysis of lactose occurred in less than 8 hours at 4° C.

Example 4

Effect of Microcarrier Density on Lactose Hydrolysis

Figure 6:
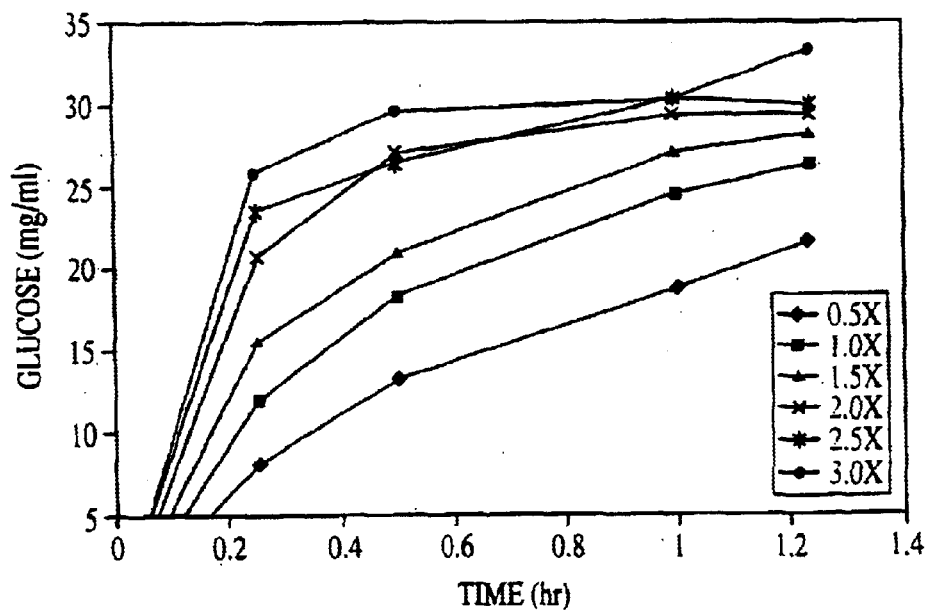
FIG. 6 is a line graph depicting the effect of *L. lactis* LM0230 (pDOC99; pDOC23) microcarrier density on lactose hydrolysis. Cells having the same β-galactosidase activities were either diluted or concentrated to 0.5 (diamond shaped), 1.0 (square shaped), 1.5 (triangle shaped), 2.0 (fine x), 2.5 heavy x), and 3.0 (circle shaped)

Cell density was found to have a significant impact on the rate of lactose hydrolysis, as indicated in FIG. 6. Cells having the same β-galactosidase activities (16,000 MU) were either diluted or concentrated to 0.5, 1.0, 1.5, 2.0, 2.5, and 3.0 times the original cell density and the rate of lactose hydrolysis measured at 55° C. in pasteurized skim milk. As the concentration of cells increased, so did the rate of lactose hydrolysis. At three times the original concentration of cells, complete hydrolysis of the lactose in milk occurred within 30 minutes.

Example 5

Effect of Per-Cell Miller Activity on Rate of Lactose Hydrolysis

The effect of the enzyme activity of individual cells was determined by growing a culture and inducing with 1.0 units/ml nisin as normal. At 30 minute intervals, aliquots of cells were removed and permeabilized following the previously described procedure of incubation in 50% ETOH. β-Galactosidase activities were measured for each aliquot and determined to be 4,508, 6,543, 10,487, and 27,248 Miller units. Each of these cell suspensions was then standardized to equal cell densities at an $OD_{600}$ of 1.6 and tested for lactose hydrolysis (FIG. 7). As the per cell activity increased, the rate of lactose hydrolysis also increased up to a maximum of approximately 10,000 Miller units. Beyond 10,000 Miller units the increase in activity had a negligible effect on the rate of lactose hydrolysis (however, in other strains, the rate of hydrolysis by the bacterium may increase with increase in Miller Unit). This would suggest that at very high per-cell activities, lactose transport across the membrane becomes a limiting factor, and therefore the permeabilization of the membrane is a limiting factor.

Example 6

Enhancement of Permeabilization of Microcarrier Cells

Following the observation that increased activity in microcarrier cells above 10,000 Miller units did not significantly increase the rate of lactose hydrolysis, several attempts were made to increase the permeability of the cell envelope. The purpose of this was to make lactose more available to the β-galactosidase enzyme, and possibly reduce the number of cells required to hydrolyze the lactose in a given volume of milk.

OXGALL® as a Permeabilization Agent

The first attempt involved the use of OXGALL™, a food-grade ox bile extract. The OXGALL™ was dissolved 1% in POM buffer, and 0.5×volume was used to resuspend pelleted cells following induction with nisin. Additional POM or 100% EtOH was then added at 0.5×volume to result in 0.5% OXGALL™ only, or 0.5% Oxgall+50% EtOH. The OXGALL™ alone resulted in very little permeabilization of the cells, as evidenced by negligible amounts of glucose upon incubation at 55° C. The OXGALL™ similarly did not enhance the permeabilization effected by the 50% EtOH, as the difference between the rates of lactose hydrolysis was negligible for the 0.5% Oxgall+50% EtOH and a 50% EtOH control incubated at 55° C.

Increased Time of Incubation with 0.5% Oxgall and 50% EtOH for Increased Permeabilization of Microcarrier Cells The length of time the cells were incubated in the permeabilizing agent was increased in an attempt to increase the level of permeabilization of the cells. Following induction with nisin, a fresh culture was aliquoted into 20 ml samples which were pelleted, washed and resuspended in 0.5×volume of 1.0% Oxgall and 0.5×volume of 100% EtOH added for a final concentration of 0.5% Oxgall and 50% EtOH. A control was also prepared with only 50% EtOH. The control and one sample were incubated for 25 minutes at RT and then washed and resuspended in POM and stored at 4° C. The remaining samples were incubated for 1, 2, and 4 hours before washing and resuspending in POM for storage at 4° C. The microcarriers were then used for lactose hydrolysis in skim milk, and the results depicted in FIG. 8. As indicated by the graph, increased incubation had no significant effect on the rate of lactose hydrolysis by the microcarrier cells.

Increased Incubation Temperature During Permeabilization for Increased Permeability of Microcarrier Cells While the specific action of the 50% EtOH is not completely understood, it is believed that various components of the cell envelope may be extracted. To increase this putative extraction, and therefore increase the permeability of the membrane, the temperature during the 50% EtOH incubation was increased to 50° C. The result of this however, was a complete loss of enzyme activity of the cells during incubation with skim milk at 55° C.

Permeabilization With Increased Nisin Concentration

Nisin is a bacteriocin that inserts into cell membranes of Gram-positive bacteria, and when six nisin molecules insert at the same position they form a channel in the membrane which kills the cell by spilling $K^+$ ions and disrupting the membrane potential. Incubation with an increased concentration of nisin was examined for permeabilization of the membrane for lactose transport. Freshly induced cells were washed and resuspended in 0.5×volume POM and 0.5× volume 100% EtOH and aliquoted into control and test samples. One percent of a 1,000 unit/ml nisin stock solution was added to the test sample for a final concentration of 10 units/ml and both were incubated at RT for 25 minutes. Both samples were then washed and resuspended in POM and stored at 4° C. The rate of lactose hydrolysis for each was tested in skim milk and the results are shown in FIG. 9. It appears that initially during the incubation, the nisin-permeated cells had a slightly higher rate of hydrolysis, but the total time required for complete hydrolysis was unaffected. This suggested that nisin may have increased the permeability of the cell slightly, but this advantage was only apparent at the high lactose concentration initially found in the milk.

Permeabilization with 35% EtOH

Permeabilization of the microcarrier cells with 35% EtOH was also tested. Freshly induced cells were aliquoted into two samples, washed and the control sample resuspended in 0.5×volume POM and the test sample in 0.65×volume POM. EtOH was added to each, 0.5×volume to the control, and 0.35×volume to the test, and both were incubated at RT for 25 min. Cells were then washed and resuspended in POM for storage at 4° C. Resuspension and incubation in skim milk indicated that the cells permeabilized with 35% EtOH hydrolyzed lactose at the same rate as cells permeabilized with 50% EtOH. Permeabilization with 50% EtOH was required, however, to completely kill the cells, as colonies appeared when the 35% EtOH-permeabilized cells were streaked on M17-G agar plates. Colonies did not appear on plates streaked with cells permeabilized with 50% EtOH, indicating complete non-viability.

Permeabilization of Concentrated Cells

Freshly induced cells were aliquoted into equal volumes, pelleted, and the supernatant discarded. A control was resuspended with 0.5×volume of POM, and test samples resuspended with 0.25×, 0.125×, and 0.05×volumes of POM. To the control 0.5×volume of 100% EtOH was added, and to the test samples 0.25×, 0.125×, and 0.05×volumes of 100% EtOH, respectively. Each was incubated at RT for 25 minutes. This resulted in a 1×control, and 2,4, and 10 times the concentration of cells being permeabilized in 50% ETOH. The cells were then washed and resuspended in the original volume of POM and stored at 4° C. Lactose hydrolysis of each sample was tested in skim milk to determine the effect of the increased concentration of cells during 50% EtOH permeabilization. For each sample of microcarrier cells the rate of lactose hydrolysis was essentially the same, there was no decrease in lactose hydrolysis when cells were concentrated for permeabilization (FIG. 10). This means that a volume of cells can be permeabilized and killed using one-tenth (or less) the original volume of 50% EtOH.

Example 7

Agitation of Cells During Lactose Hydrolysis

The purpose of this experiment was to increase lactose transport across the cell membrane by stirring the milk/microcarrier suspension rather than increasing the permeability of the cell. Cells that had been previously induced and permeabilized were pelleted and resuspended in skim milk and incubated at 55° C., one sample shaking in a dry shaking incubator at 225 rpm, while a control was incubated on a stationary shelf in the same incubator. The results of the experiment are shown in FIG. 11. As the graph indicates, the initial rate of lactose a hydrolysis was greater in the agitated sample, the level of glucose in this suspension was 50% greater than that found in the stationary milk after 15 minutes of incubation. The total time for complete hydrolysis was essentially the same however. This is very similar to the result observed when nisin was used to increase permeabilization of the cell. These measures provided an enhancement at very high concentrations of lactose, but as the lactose was depleted, permeability of the cell was no longer a limiting factor.

Example 8

Growth and Induction of Cells in a 1 Liter External Controlled pH Fermenter

The production of the β-galactosidase enzyme in a whey-based media in an external pH-controlled fermenter was examined. This media is less costly than commercial broth media, and the possibility of increasing cell density through external-controlled pH could produce more cells for lactose hydrolysis than a normal batch culture.

Preparation of a Whey-Based Media

To prepare the whey-based media in accordance with the manufacturer's directions, 70 g of non-fat milk solids were added to 1 L of $H_2O$ The solution was mixed and tempered to 57° C. The pH was adjusted to 7.0 with ammonium hydroxide and 4.2 ml of a solution of the provided protease (1 g/20 ml $H_2O$) added. The solution was incubated at 57° C. for digestion of the whey proteins to provide short-chain polypeptides and free amino acids for the organisms. Next, 9.0 g of yeast extract, 0.3 g of manganous chloride, and 0.2 g ferrous sulfate were added. The solution was poured into the fermentation vessel and autoclaved at 121° C. for 15 minutes.

Growth Conditions in the External-pH-Controlled Fermenter

The lactococcal cells were grown and induced in the external-pH-controlled fermenter under the following conditions:

Digested Whey Protein Media

Chloramphenicol 3 µg/ml; Erythromycin 3µg/ml

30° C.

Stirring 300 rpm pH 6.3–6.4—pH maintained with 4M ammonium hydroxide

No gassing

A sample was removed for β-galactosidase activity and cell count. The culture was then induced with nisin by adding 1.0 ml of a 1000 unit/ml stock solution of PerLac for a final concentration of 1.0 units/ml nisin in the growth media. During the induction period samples were removed for cell count and β-galactosidase activity.

The whey based media had a very opaque caramel color, making $OD_{600}$ determinations impossible. In order to calculate Miller activity units cell counts were determined by viable plate counts on M17-G agar plates, dilutions were made in 0.85% saline. $OD_{600}$ estimates were calculated from a standard curve of $OD_{600}$ versus cell count. A maximum of ~22,000 Miller units was observed 2.5 hours after induction with nisin.

Example 9

L. Lactis Growth and β-galactosidase Production in Super MRS Media Using 2 Liter Fermenter Food-grade version of L. lactis strain NZ3900-pNZ8037.LacZ was produced by replacing the antibiotic resistance markers with a Lacf gene (0355036 A1). The resulting plasmid was introduced into L. lactis strain NZ3900 (European Patent Application 0355036 A1) which contains chromosomal LacZ operon with a Lacf mutation. The L. lactis strain NZ3900-pNZ8037. LacZ was grown for β-galactosidase production in 2 liter fermenter using 10% lactose containing Super MRS media (0.5% Tryptone, 0.5% Soytone, 1.5% Yeast extract, 0.2% Ammonium citrate, 0.2% Potassium phosphate, 0.02% Magnesium Sulfate, and 0.005% Manganese sulfate). 0.5 unit of nisin inducer was added per ml culture at $OD_{600}$=4.6 and the fermentation was completed in 3 hours. Final cell density was 8.45 at $OD_{600}$ nm.

Cells were harvested by centrifuging at 8,000 rpm for 20 minutes. The harvested cells were treated with 250 ml of 50% ethanol-POM buffer for cell inactivation and permeabilization. Total enzyme activity was 83,111 ONPG units per ml of cell culture. Comparing the L. lactis LM0230 (pDOC23:pDOC99) strain, the L. lactis strain NZ3900 produced about 4 times more β-galactosidase.

Thus, the L. lactis LM0230 (pDOC23:pDOC99) and NZ3900-pNZ8037.LacZ constructs produce the β-galactosidase enzyme following induction with 0.5–1.0 IU nisin/ml in excess at an approximate maximum of 30,000 Miller units in M17 plus 0.5% glucose or 10% lactose. These cells can then be treated with 50% EtOH to kill and permeabilize them and be used as enzyme microcarriers to hydrolyze the lactose in milk to the digestible monosaccharides glucose and galactose.

The intact cells are required to protect the β-galactosidase enzyme from proteases, but they must be permeabilized to allow transport of lactose into the cells. The most effective method examined for permeabilization was room temperature incubation of cells suspended in 50% EtOH, which also renders the cells non-viable. Permeabilization was also achieved by incubation in 35% EtOH, however cells were able to survive this treatment. Increasing the cell density during 50% incubation had no negative effect on the efficacy of permeabilization.

The permeabilized bacteria generated herein have high local concentrations of β-galactosidase which can, surprisingly, hydrolyze lactose efficiently over an extended temperature range. Using the L. lactis strain LM0230 (pDOC23:pDOC99), lactose hydrolysis in skim milk was achieved in less than one hour by resuspending cells in milk and incubating at 55° C. (FIG. 14). Hydrolysis was also achieved by incubation of the milk/microcarrier suspension at 4° C. in less than 8 hours with agitation to keep the cells in suspension (FIG. 13). In addition, these bacteria can hydrolyze lactose at a unexpectedly fast rate as compared to known wild-type lactic acid bacteria For example, L. lactis strain LM0230 (pDOC23:pDOC99) at 4° C., hydrolyzes lactose at a similar rate as wild-type St. thermophilus at 55° C. (FIG. 12).

Example 10

Lactose Microcarriers as an Oral Prophylactic Against the Clinical Condition of Lactose Intolerance In vitro experiments were carried out to examine treatment effects of simulated intestinal juice containing pancreatic enzymes and bile on the enzyme activities of commercial soluble lactase and lactase microcarriers.

Simulated intestinal fluid treatment of two lactase preparations, including a commercial soluble yeast lactase product (Maxilact 2000, Gist Brocades) and lactase microcarriers prepared as described herein, was carried out using a porcine pancreatic enzyme mixture at pH 8.0. Reactions were started by the mixing of approximately 500 units of Maxilact, a soluble yeast enzyme used in milk processing and prophylactic applications, or lactase microcarriers to 5.0 ml of simulated intestinal fluid (0.5% NaCl at pH 8.0; 37° C.) containing 0.1% Pancreatin U.S.P. (Sigma). Parallel reactions were carried out both with and without bile salts (0.1%; Sigma). Samples in each case were taken at 10–20 minute intervals and the reaction of proteases was quenched by the addition of 0.1 ml of incubation mix to 0.4 ml of 0.1 M phosphate buffer pH 7.0+1.0 mM $MgSO_4$+50 mM BME (Z Buffer) containing 5.0 mg/ml of bovine serum albumin. Quenched samples were refrigerated until enzyme activity assays were performed shortly thereafter.

The beta-galactosidase activity levels of control (untreated) and intestinal fluid treated samples were assayed using ONPG as substrate in the Miller assay protocol (Experiments In Molecular Genetics, J. H. Miller, Cold Spring Harbor Press, Cold Spring Harbor, N.Y. 1977; p. 352). Reactions were carried out using enzyme dilutions that produced a maximum $OD_{420}$=1.2 after 5.0 minutes at 28° C. Reactions were stopped by the addition of 1.0 M $NaCO_3$ and the amount of ONPG hydrolyzed measured spectrophotometrically by recording absorbance at 420 nanometers. The percent enzyme activity remaining in control and treated samples was calculated relative to either soluble or microcarrier samples sampled at time "0".

Results show that the beta-galactosidase present in lactase microcarriers appears to be significantly more resistant to the effects of simulated intestinal fluid than Maxilact. Lactase microcarriers were resistant to the proteolytic enzymes including trypsin and chymotrypsin present in Pancreatin (FIG. 16) and appeared unaffected as well by the addition of 0.1% bile salts (FIG. 17). In contrast, to soluble lactase which lost >95% of its activity in the first 10 minutes of incubation with intestinal fluid, Microcarriers appeared to be impermeable to pancreatic digestive enzymes and retained their integrity, even in the presence of the detergent effects of 0.1% bile. Microcarriers, in fact, demonstrated a slight increase in activity during the 60 minute incubation with intestinal fluid, which suggests that the action of pancreatic enzymes may serve to increase the permeability of microcarrier membranes and increase the accessibility of small molecules like ONPG and lactose to enzyme within.

Experimental observations from human feeding studies have shown that as much as 90% of lactose present in yogurt fed to lactase-deficient volunteers is digested while transiting the small intestine, the normal site for lactose hydrolysis and absorption in individuals with elevated intestinal lactase levels (Brit. J. of Nutrition, 64:71–79, 1990). Since lactase microcarriers were shown to resist the degradative conditions found in the small intestine, it is likely that microcarriers can be more effective in degrading lactose when delivered to the small intestine as a prophylactic product.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for preparing a lactase microcarrier for hydrolyzing lactose in a liquid, the method comprising:

transforming a food-grade lactic acid bacterium with a DNA construct, wherein the DNA construct comprises a lantibiotic promoter sequence operatively linked to a DNA sequence encoding a β-galactosidase;

culturing the bacterium under conditions that enable expression of the β-galactosidase in an amount sufficient exhibit a β-galactosidase activity of at least 4000 Miller Units; and permeabilizing the bacterium, wherein a preparation of permeabilized bacteria equal to about 1.55 at $OD_{600}$ can hydrolyze either (i) about 100% of lactose in skim milk at a temperature of about 55° C. within two to three hours, (ii) about 50% of lactose in skim milk at a temperature of 4° C. within two to three hours, or (iii) both (i) and (ii).

2. The method of claim 1, wherein the lactic acid bacterium is selected from the group consisting of Streptococcus, Aerococcus, Carnobacterium, Enteroccus, Erysipelothrix, Gemella, Globicatella, Lactobacillus, Lactococcus, Bifodobacteria, Leuconostoc, Pediococcus, Tetragenococcus, and Bagococcus bacteria.

3. The method of claim 1, wherein the lactic acid bacterium is a *Lactococcus lactis*.

4. The method of claim 1, wherein the DNA sequence encoding β-galactosidase is from a *Streptococcus thermophilus, Lactobacillus bulgaricus, Bifobacterium species, Aspergillus niger, Aspergillus oryzae, Kluyveromyces fragilis, Kluyveromyces lactis, Bacillus subtillus* or *Arthrobacter* species.

5. The method of claim 1, wherein the promoter is a nisin gene promoter.

6. The method of claim 1, wherein the promoter is a nisA promoter.

7. The method of claim 1, wherein the bacterium is permeabilized by an agent selected from the group consisting of a chemical, a solvent, and a detergent.

8. The method of claim 1, wherein the bacterium is permeabilized by ethanol, isopropanol, or a combination of ethanol and isopropanol.

9. The method of claim 7, wherein the detergent is selected from the group consisting of deoxycholate, sodium dodecyl sulfate, rhamnolipid, and chenodeoxycholate.

10. The method of claim 1, wherein the bacterium exhibits a β-galactosidase activity of at least 10,000 Miller Units.

11. A perneabilized lactic acid bacterium containing a heterologous β-galactosidase, wherein the bacterium exhibits a β-galactosidase activity of at least about 4000 Miller Units, and wherein a preparation of permeabilized bacteria equal to about 1.55 at $OD_{600}$ can hydrolyze either (i) about 100% of lactose in skim milk at a temperature of about 55° C. within two to three hours, (ii) about 50% of lactose in skim milk at a temperature of 4° C. within two to three hours, or (iii) both (ii and (ii).

12. The permeabilized bacterium of claim 11, wherein the bacterium is selected from the group consisting of Streptococcus, Aerococcus, Carnobacterium, Enteroccus, Erysipelothrix, Gemella, Globicatella, Lactobacillus, Lactococcus, Bifidobacteria, Leuconostoc, Pediococcus, Tetragenococcus, and Bagococcus bacteria.

13. The permeabilized bacterium of claim 11, wherein the bacterium is a *Lactococcus lactis*.

14. The permeabilized bacterium of claim 11, wherein the β-galactosidase is a *Streptococcus thermophilus* β-galactosidase.

15. The permeabilized bacterium of claim 11, wherein the bacterium is in a lyophilized form, in a concentrated cell suspension, or immobilized.

16. A composition comprising the permeabilized bacterium of claim 11.

* * * * *